(12) United States Patent
Rasochova et al.

(10) Patent No.: US 11,590,149 B2
(45) Date of Patent: *Feb. 28, 2023

(54) COMPOSITIONS AND METHODS FOR TREATING ACNE VULGARIS

(71) Applicant: Dermala, Inc., San Diego, CA (US)

(72) Inventors: Lada Rasochova, Del Mar, CA (US); Michelle Kem, San Diego, CA (US)

(73) Assignee: Dermala, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/461,146

(22) Filed: Aug. 30, 2021

(65) Prior Publication Data
US 2022/0079958 A1 Mar. 17, 2022

Related U.S. Application Data

(63) Continuation of application No. 17/327,559, filed on May 21, 2021, which is a continuation of application No. 16/302,637, filed as application No. PCT/US2017/033346 on May 18, 2017, now Pat. No. 11,040,046.

(60) Provisional application No. 62/470,130, filed on Mar. 10, 2017, provisional application No. 62/338,334, filed on May 18, 2016.

(51) Int. Cl.
| | | |
|---|---|---|
| *A61K 31/60* | (2006.01) | |
| *A61P 17/10* | (2006.01) | |
| *A61K 9/00* | (2006.01) | |
| *A61K 9/06* | (2006.01) | |
| *A61K 9/70* | (2006.01) | |
| *A61K 31/194* | (2006.01) | |
| *A61K 31/20* | (2006.01) | |
| *A61K 31/327* | (2006.01) | |
| *A61K 31/4402* | (2006.01) | |
| *A61K 33/30* | (2006.01) | |
| *A61K 35/745* | (2015.01) | |
| *A61K 35/747* | (2015.01) | |
| *A61K 36/752* | (2006.01) | |
| *A61K 36/886* | (2006.01) | |
| *A61K 45/06* | (2006.01) | |
| *A61K 47/44* | (2017.01) | |
| *A61K 47/10* | (2017.01) | |
| *A61K 8/36* | (2006.01) | |
| *A61K 8/362* | (2006.01) | |
| *A61Q 19/00* | (2006.01) | |

(52) U.S. Cl.
CPC ............ *A61K 31/60* (2013.01); *A61K 8/36* (2013.01); *A61K 8/362* (2013.01); *A61K 9/0014* (2013.01); *A61K 9/06* (2013.01); *A61K 9/7007* (2013.01); *A61K 31/194* (2013.01); *A61K 31/20* (2013.01); *A61K 31/327* (2013.01); *A61K 31/4402* (2013.01); *A61K 33/30* (2013.01); *A61K 35/745* (2013.01); *A61K 35/747* (2013.01); *A61K 36/752* (2013.01); *A61K 36/886* (2013.01); *A61K 45/06* (2013.01); *A61K 47/10* (2013.01); *A61K 47/44* (2013.01); *A61P 17/10* (2018.01); *A61Q 19/00* (2013.01)

(58) Field of Classification Search
CPC ........ A61K 31/60; A61K 45/06; A61K 47/44; A61K 47/10; A61K 8/36; A61K 8/362; A61K 9/0014; A61K 9/06; A61K 9/7007; A61K 31/194; A61K 31/20; A61K 31/327; A61K 31/4402; A61K 33/30; A61K 35/745; A61K 35/747; A61K 36/752; A61K 36/886; A61Q 19/00; A61P 17/10

See application file for complete search history.

(56) References Cited

U.S. PATENT DOCUMENTS 9,101,662 B2 * 8/2015 Tamarkin ............. A61K 31/167

* cited by examiner

*Primary Examiner* — Sahar Javanmard
(74) *Attorney, Agent, or Firm* — Torrey Pines Law Group, PC

(57) ABSTRACT

Disclosed are compositions, methods of treatment using the compositions and methods of preparing the compositions for the treatment of acne vulgaris. The compositions include succinic acid and an API selected from the group consisting of salicylic acid, azelaic acid, picolinic acid, benzoyl peroxide, antibiotic, retinoid and combinations thereof in a pharmaceutically acceptable preparation. The compositions that include the combination of succinic acid and another API produce improved efficacy in treating acne vulgaris.

16 Claims, 18 Drawing Sheets

|   | 1 | 2 | 3 | 4 | 5 | 6 | 7 | 8 |
|---|---|---|---|---|---|---|---|---|
| A | 1/8 | 1/16 | 1/32 | 1/64 | 1/128 | 1/256 | 1/512 | 0 |
| B | 1/4 | 1/8 | 1/16 | 1/32 | 1/64 | 1/128 | 1/256 | 0 |
| C | 1/2 | 1/4 | 1/8 | 1/16 | 1/32 | 1/64 | 1/128 | 0 |
| D | 1 | 1/2 | 1/4 | 1/8 | 1/16 | 1/32 | 1/64 | 0 |
| E | 2 | 1 | 1/2 | 1/4 | 1/8 | 1/16 | 1/32 | 0 |
| F | 4 | 2 | 1 | 1/2 | 1/4 | 1/8 | 1/16 | 0 |
| G | 8 | 4 | 2 | 1 | 1/2 | 1/4 | 1/8 | 0 |
| H | N/A | N/A | N/A | N/A | N/A | N/A | N/A | N/A |

FIG. 7

DRM1 increasing concentrations →

Picolinic acid increasing concentrations ↓

|   | 1 | 2 | 3 | 4 | 5 | 6 | 7 | 8 |
|---|---|---|---|---|---|---|---|---|
| A | 250 / 7085 | 125 / 7085 | 62.5 / 7085 | 31.25 / 7085 | 15.6 / 7085 | 7.8 / 7085 | 3.9 / 7085 | 0 / 7085 |
| B | 250 / 3542 | 125 / 3542 | 62.5 / 3542 | 31.25 / 3542 | 15.6 / 3542 | 7.8 / 3542 | 3.9 / 3542 | 0 / 3542 |
| C | 250 / 1771 | 125 / 1771 | 62.5 / 1771 | 31.25 / 1771 | 15.6 / 1771 | 7.8 / 1771 | 3.9 / 1771 | 0 / 1771 |
| D | 250 / 885.7 | 125 / 885.7 | 62.5 / 885.7 | 31.25 / 885.7 | 15.6 / 885.7 | 7.8 / 885.7 | 3.9 / 885.7 | 0 / 885.7 |
| E | 250 / 442.8 | 125 / 442.8 | 62.5 / 442.8 | 31.25 / 442.8 | 15.6 / 442.8 | 7.8 / 442.8 | 3.9 / 442.8 | 0 / 442.8 |
| F | 250 / 221.4 | 125 / 221.4 | 62.5 / 221.4 | 31.25 / 221.4 | 15.6 / 221.4 | 7.8 / 221.4 | 3.9 / 221.4 | 0 / 221.4 |
| G | 250 / 110.7 | 125 / 110.7 | 62.5 / 110.7 | 31.25 / 110.7 | 15.6 / 110.7 | 7.8 / 110.7 | 3.9 / 110.7 | 0 / 110.7 |
| H | 250 / 0 | 125 / 0 | 62.5 / 0 | 31.25 / 0 | 15.6 / 0 | 7.8 / 0 | 3.9 / 0 | 0 / 0 |

DRM1 increasing concentrations ←

BPO increasing concentrations →

FIG. 8

| | |
|---|---|
| E | S. Epidermidis Sucrose Fermentation Dermala 4/28/17 |
| D | S. Epidermidis Maltose Fermentation Dermala 4/28/17 |
| C | S. Epidermidis Lactose Fermentation Dermala 4/28/17 |
| B | S. Epidermidis Glycerol Fermentation Dermala 4/28/17 |
| A | S. Epidermidis CTRL Fermentation 4/28/17 Dermala |

FIG. 17

COMPOSITIONS AND METHODS FOR TREATING ACNE VULGARIS

CROSS-REFERENCE TO RELATED APPLICATIONS

This application is a Continuation of U.S. application Ser. No. 17/327,559, filed on May 21, 2021, which is a Continuation of U.S. application Ser. No. 16/302,637, filed on Nov. 17, 2018, which is a National Stage Entry of PCT Application No. PCT/US2017/033346, filed on May 18, 2017, and which claims priority to U.S. Provisional Application Ser. No. 62/338,334 filed on May 18, 2016, and U.S. Provisional Application Ser. No. 62/470,130 filed on Mar. 10, 2017, all of which are incorporated herein by reference in its entirety.

STATEMENT REGARDING FEDERALLY SPONSORED RESEARCH OR DEVELOPMENT

Not applicable.

FIELD

The present invention is related to compositions and methods for the treatment of acne vulgaris and, in particular, to topical compositions and methods based upon compositions that are combinations of succinic acid and one or more of topical API including retinoid, salicylic acid, azelaic acid, picolinic acid, benzoyl peroxide, or antibiotic, in a pharmaceutically acceptable preparation.

INTRODUCTION

Acne is a significant inflammatory skin disorder and it is considered the most common skin disorder. There are four disease factors associated with acne vulgaris. They include sebum overproduction, follicular hyperkeratinization, *Propionibacterium acnes* (*P. acnes*) proliferation in hair follicles, and inflammation. Acne affects about 50 million people in the US. It is highly common among adolescents, affecting up to 95% of men and 83% of women in that age group. In approximately 10% of cases, acne has been reported to become severe nodulocystic acne with the potential of producing lifelong disfiguring scars. Acne lesions typically recur for years. Therefore, acne is considered a chronic disease.

The psychosocial morbidity associated with acne is important and includes depression and suicidal thoughts. In addition to impact on patient's quality of life, the economic burden of acne treatment is significant.

Currently available treatments for acne are insufficient. Treatment options against acne vulgaris typically only address one or two disease factors—*P. acnes* proliferation and follicular hyperkeratinization. Treatment options for acne vulgaris suffer from significant side effects and none provides complete protection. Potential side effects include skin irritation including burning, erythema, peeling, dryness, and contact allergy. Antibiotics pose various side effects that range from colitis, vaginal candidiasis, and photosensitivity to the development of bacterial resistance and cross-resistance.

Thus, there is a need to develop new therapies with reduced side effects and therapies that address multiple acne vulgaris disease factors—*P. acnes* proliferation, follicular hyperkeratinization, and inflammation.

SUMMARY

Accordingly, the applicants herein have succeeded in devising new formulations and methods for treating acne vulgaris.

Thus, in various embodiments, the present invention includes a topical composition for treating acne vulgaris in which the composition includes a combination of succinic acid and salicylic acid in a pharmaceutically acceptable preparation. The combination of succinic acid and salicylic acid acts in a synergistic manner in killing *Propionibacterium acnes* (*P. acnes*) and treating acne vulgaris, requires ¼ of the dose of succinic acid and salicylic acid to be effective in killing *P. acnes* and treat acne vulgaris and it is faster acting compared to succinic acid or salicylic acid alone. In various other embodiments, the present invention includes a topical composition for treating acne vulgaris in which the composition includes a combination of succinic acid and an API that may be topical retinoid, salicylic acid, azelaic acid, picolinic acid, benzoyl peroxide, antibiotics or combinations thereof, in a pharmaceutically acceptable preparation. The combination of succinic acid and BPO, succinic acid and azelaic acid, and succinic acid and picolinic acid acts in additive manner against *P. acnes* and requires ½ of the dose of individual components to kill *P. acnes* and treat acne vulgaris. The combination of succinic acid and antibiotic prevents antibiotic resistance development and is effective in treating acne vulgaris associated with antibiotic resistant *P. acnes*. Any combinations containing succinic acid prevent *P. acnes* biofilm development in follicles.

In various other embodiments, the present invention includes a method of treating acne vulgaris. The method includes administering to a subject in need thereof, a topical composition comprising a combination of succinic acid and another API, such as retinoid, salicylic acid, azelaic acid, picolinic acid, benzoyl peroxide, or antibiotic, in a pharmaceutically acceptable preparation.

In various additional embodiments, the present invention includes a method of preparing a topical formulation for treatment of acne vulgaris. The method includes combining succinic acid with another API in a pharmaceutically acceptable preparation, wherein the combination of succinic acid and another API produces additional effect in treating acne vulgaris, including synergistic or additive effect against *P. acnes*, prevention of antibiotic resistance development, prevention of *P. acnes* biofilm formation, or faster acting pharmaceutical composition.

In various embodiments, the present invention includes a topical composition for treating acne vulgaris. The composition may include succinic acid and an API that may be topical retinoid, salicylic acid, azelaic acid, picolinic acid, benzoyl peroxide, antibiotics or combinations thereof, in a pharmaceutically acceptable preparation.

In various other embodiments, the present invention includes a method of treating acne vulgaris. The method includes administer to a subject in need thereof, a topical composition that may include succinic acid and an API selected from the group consisting of topical retinoids, salicylic acid, azelaic acid, picolinic acid, benzoyl peroxide, clindamycin and combinations thereof in a pharmaceutically acceptable preparation.

In various other embodiments, the present invention includes a method of treating inflammatory acne vulgaris that contains a topical composition that includes succinic acid and another component API selected from the group consisting of topical retinoids, salicylic acid, azelaic acid, picolinic acid, benzoyl peroxide, clindamycin and combinations thereof in a pharmaceutically acceptable preparation.

In various additional embodiments, the present invention includes a method of preparing a topical formulation for treatment of acne vulgaris. The method includes combining succinic acid and an API selected from the group consisting of retinoids, salicylic acid, azelaic acid, picolinic acid, benzoyl peroxide, antibiotics, and combinations thereof in a pharmaceutically acceptable preparation.

In various embodiments, the compositions and preparations above can be provided to a subject in a pad, tube, and any container suitable for the delivery of the compositions and preparations so a subject.

These and other features, aspects and advantages of the present teachings will become better understood with reference to the following description, examples and appended claims.

DRAWINGS

Those of skill in the art will understand that the drawings, described below, are for illustrative purposes only. The drawings are not intended to limit the scope of the present teachings in any way.

FIG. 1 illustrates checkerboard assay using *P. acnes* for concentrations (mM) of succinic acid and salicylic acid used in each well in which the boxes highlighted in yellow (in the applications from which this application depends; C8 and H3 here) are the individual MIC values for each API; the green box (in the applications from which this application depends; C3) indicates where the concentrations of the individual MIC values intersect; the orange box (in the applications from which this application depends; E5) indicates the new MIC value obtained by the combination of succinic acid and salicylic acid; the boxes shaded in grey indicate bacterial growth; and the white boxes indicate no growth.

FIG. 2 illustrates the ratios of salicylic acid to succinic acid determined by checkerboard assay using *P. acnes* in which the boxes highlighted in yellow (in the applications from which this application depends; C8 and H3 here) are the individual MIC values for each API; the green box (in the applications from which this application depends; C3) indicates where the concentrations of the individual MIC values for each API intersect; the orange box (in the applications from which this application depends; E5) indicates the new MIC value obtained by the combination of succinic acid and salicylic acid; the boxes shaded in grey indicate bacterial growth; and the white boxes indicate no growth.

FIG. 3 illustrates a time-kill assay comparing succinic acid individually to succinic acid and salicylic acid combination in which each plate shows four dilutions for each time point starting with 1:10 (right) and ending with $1:10^4$ (left).

FIG. 4 illustrates checkerboard assay using *P. acnes* for concentrations (mM) of succinic acid and azelaic acid used in each well in which the boxes highlighted in yellow (in the applications from which this application depends; H3 and C8 here) are the individual MIC values for each API; the green box (in the applications from which this application depends; C3) indicates where the concentrations of the individual MIC values intersect; the orange box (in the applications from which this application depends; D4) indicates the new MIC value obtained by the combination of succinic acid and azelaic acid; the boxes shaded in grey indicate bacterial growth; and the white boxes indicate no growth.

FIG. 5 illustrates the ratios of azelaic acid to succinic acid determined by checkerboard assay using *P. acnes* in which the boxes highlighted in yellow (in the applications from which this application depends; H3 and C8 here) are the individual MIC values for each API; the green box (in the applications from which this application depends; C3) indicates where the concentrations of the individual MIC values intersect; the orange box (in the applications from which this application depends; D4) indicates the new MIC value obtained by the combination of succinic acid and azelaic acid; the boxes shaded in grey indicate bacterial growth; and the white boxes indicate no growth.

FIG. 6 illustrates checkerboard assay using *P. acnes* for concentrations (mM) of succinic acid and picolinic acid used in each well in which the boxes highlighted in yellow (in the applications from which this application depends; H3 and C8 here) are the individual MIC values for each API; the green box (in the applications from which this application depends; C3) indicates where the concentrations of the individual MIC values intersect and the orange box (in the applications from which this application depends; D4) indicates the new MIC value obtained by the combination of succinic acid and picolinic acid. The boxes shaded in grey indicate bacterial growth and white boxes indicate no growth.

FIG. 7 illustrates the ratios of picolinic acid to succinic acid determined by checkerboard assay in which the boxes highlighted in yellow (in the applications from which this application depends; H3 and C8 here) are the individual MIC values for each drug; the green box (in the applications from which this application depends; C3) indicates where the concentrations of the individual MIC values intersect; the orange box (in the applications from which this application depends; D4) indicates the new MIC value obtained by the combination of succinic acid and picolinic acid; the boxes shaded in grey indicate bacterial growth; and the white boxes indicate no growth.

FIG. 8 illustrates checkerboard assay using *P. acnes* for concentrations (mM) of succinic acid and benzoyl peroxide used in each well in which the boxes highlighted in yellow (in the applications from which this application depends; H2 and C8 here) are the individual MIC values for each API; the green box (in the applications from which this application depends; C2) indicates where the concentrations of the individual MIC values intersect; the orange box (in the applications from which this application depends; D3) indicates the new MIC value obtained by the combination of succinic acid and benzoyl peroxide; the boxes shaded in grey indicate bacterial growth; and the white boxes indicate no growth.

FIG. 9 illustrates the ratios of benzoyl peroxide to succinic acid determined by checkerboard assay in which the boxes highlighted in yellow (in the applications from which this application depends H2 and C8 here) are the individual MIC values for each API; the green box (in the applications from which this application depends; C2) indicates where the concentrations of the individual MIC values intersect; the orange box (in the applications from which this application depends; D3) indicates the new MIC value obtained by the combination of succinic acid and benzoyl peroxide; the boxes shaded in grey indicate bacterial growth; and the white boxes indicate no growth.

FIG. 10. illustrates checkerboard assay using *P. acnes* for concentrations (mM) of succinic acid and clindamycin used in each well in which the boxes highlighted in yellow (in the applications from which this application depends; H3 and C8 here) are the individual MIC values for each API; the green box (in the applications from which this application depends; C3) indicates where the concentrations of the individual MIC values intersect and the orange box indicates the new MIC value obtained by the combination of succinic acid and clindamycin; the boxes shaded in grey indicate bacterial growth; and the white boxes indicate no growth.

FIG. 11 illustrates the ratios of clindamycin to succinic acid determined by checkerboard assay in which the boxes highlighted in yellow (in the applications from which this application depends; H3 and C8 here) are the individual MIC values for each API; the green box (in the applications from which this application depends; C3) indicates where the concentrations of the individual MIC values intersect; the boxes shaded in grey indicate bacterial growth; and the white boxes indicate no growth.

FIG. 12 illustrates that succinic acid kills antibiotic resistant *P. acnes* strains in assay in which succinic acid was tested against *P. acnes* strains RMA#20660 (black) and RMA#20661 (grey) with resistance to erythromycin, clindamycin, minocycline and doxycycline: wherein the DRM1 (succinic acid) MIC value (determined at 15 mM for each strain) was defined as ≥90% decrease in bacterial growth as monitored at an optical density of 600 nm and the results reported as the mean of three individual experiments where ND means not detected and clindamycin showed no ability to inhibit RMA#20660 or RMA#20661 strains.

FIG. 17 shows production of SE Microbiome Complex by *S. epidermidis* fermentation with selected prebiotic compounds.

Figure 1:
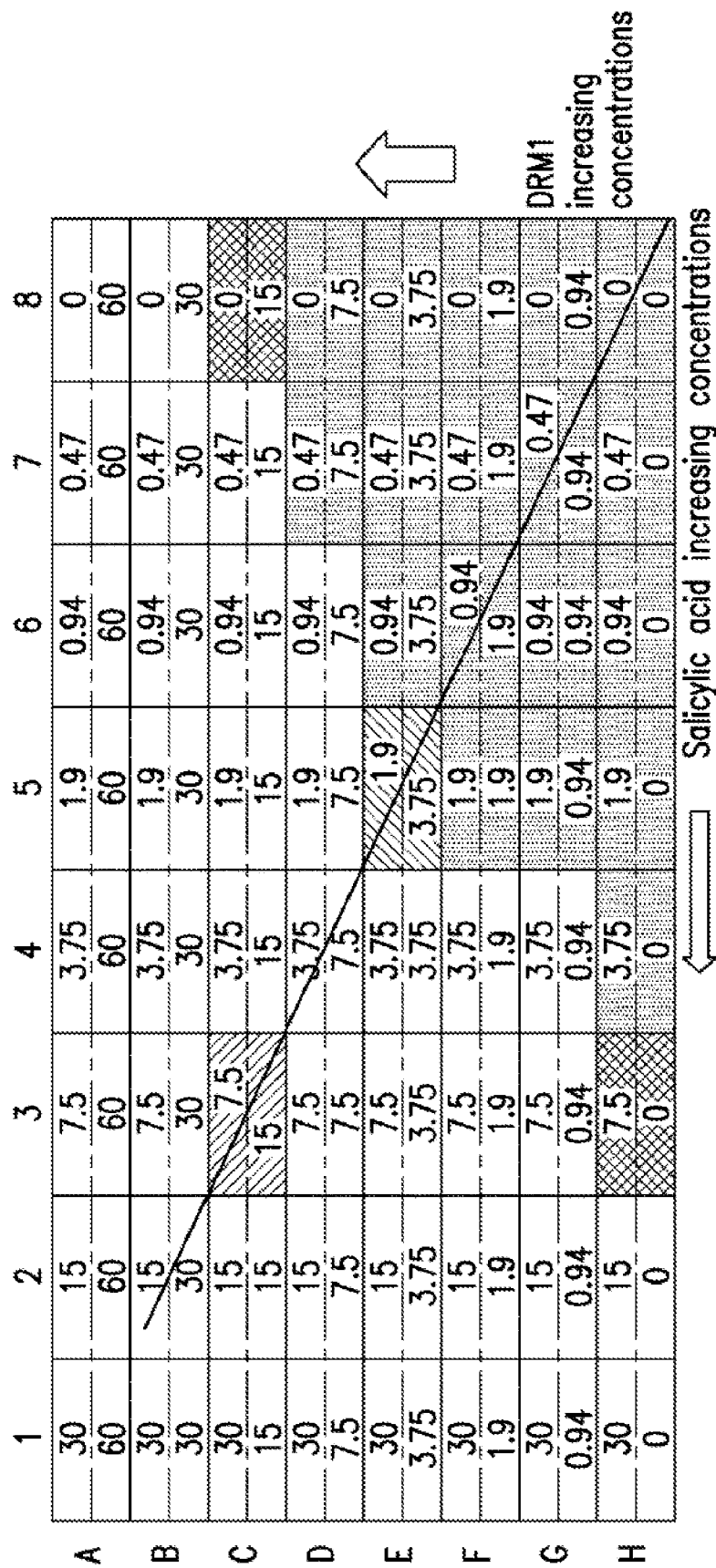
Figure 18B:
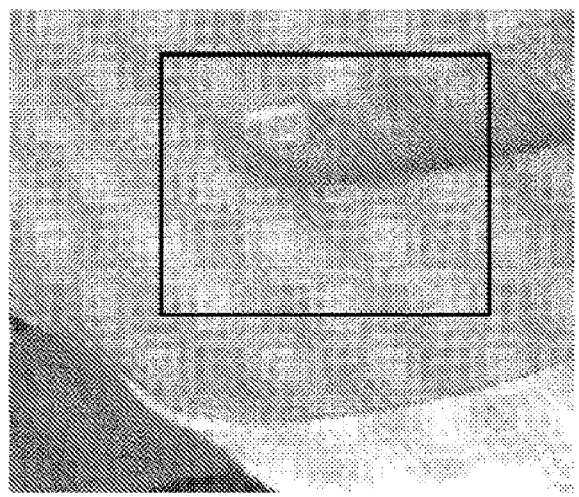
Figure 18A:
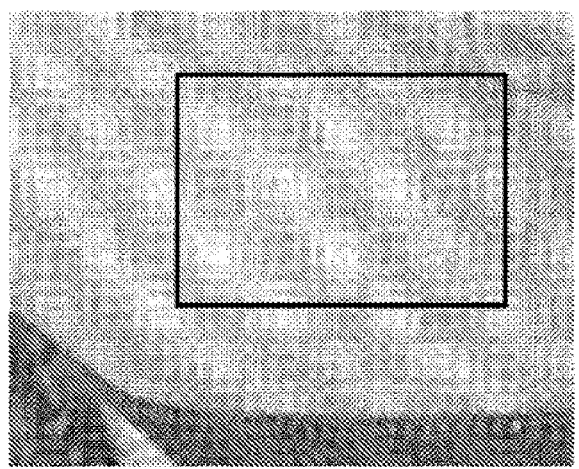
Figure 18:
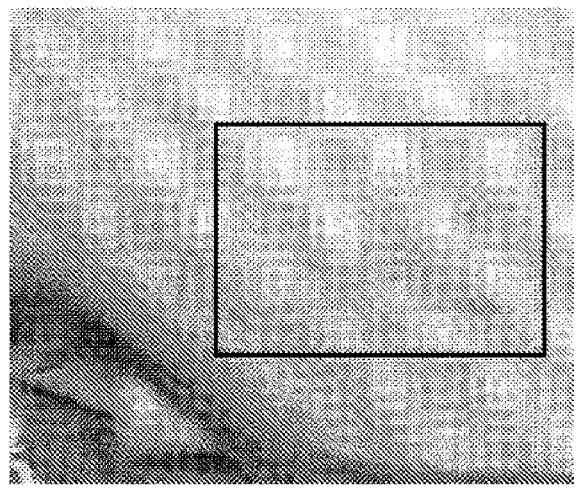

FIG. 18, FIG. 18A and FIG. 1_8B show healing of acne in a human subject after application of Formulation 1.

DETAILED DESCRIPTION

The present invention includes compositions and methods directed to the treatment of skin diseases, and in particular, inflammatory acne vulgaris. The compositions as well as treatment and formulation methods are based upon combinations of agents with antimicrobial, anti-hyperkeratinization, anti-comedogenic, and anti-inflammatory effects that are effective in treating acne vulgaris.

Abbreviations and Definitions

To facilitate understanding of the invention, a number of terms and abbreviations as used herein are defined below as follows:

As used herein, the singular forms "a", "an", and "the" include plural referents unless the context clearly dictates otherwise. Thus, for example, reference to "a formulation" includes a plurality of such formulations and reference to "the method" includes reference to one or more methods and equivalents thereof known to those skilled in the art, and so forth.

As used herein, the term "about" is intended to refer to a range of values above and below a stated value such as for example, values encompassing 10% below up to 10% above a stated value.

The term "and/or" is intended to mean either or both of two recited elements.

"Active pharmaceutical ingredient" ("API") refers to a substance, in particular an antimicrobial agent, in a pharmaceutical composition that is delivered for a desired effect.

As used herein, the term "combination" with respect to active agents refers to a composition of two or more active agents, in particular, agent with antimicrobial and/or anti-inflammatory and/or anti-hyperkeratinization and anti-comedogenic effects. In the present invention, a combination of active agents may include succinic acid and an API that may include retinoid, salicylic acid, azelaic acid, picolinic acid, benzoyl peroxide, antibiotic, and combinations of two or more API's.

Reference herein to an API including, but not limited to succinic acid, retinoids, salicylic acid, azelaic acid, picolinic acid, benzoyl peroxide and antibiotics is intended to include pharmaceutically acceptable solvates, salts, hydrates or hydrated salts, their optical isomers, racemates, diastereomers, enantiomers or the polymorphic crystalline structures of the compounds.

In the Examples below, DRM1 refers to succinic acid.

The term "pharmaceutical composition" or "pharmaceutical preparation" refers to a composition that combines one or more API's with a pharmaceutically acceptable carrier such that the composition is suitable for therapeutic use in vitro, in vivo or ex vivo.

As used herein, the term "pharmaceutically acceptable carrier" encompasses any suitable pharmaceutical carriers, such as a phosphate buffered saline solution, water, and emulsions, such as an oil/water or water/oil emulsion, various types of wetting agents and the like. The compositions also can include stabilizers and preservatives. Examples of carriers, stabilizers and adjuvants, can be found in Remington: The Science and Practice of Pharmacy, Lippincott Williams & Wilkins, Twenty-First edition (May 19, 2005).

A number of carrier systems have been developed, in particular for topical application, including by way of non-limiting examples, vesicular systems such as liposomes, niosomes, ethosomes and transfersomes. (Arora, S. et al., Dermal delivery of drugs using different, vesicular carriers: A comparative review, J Pharm. 2012; 6:237-44).

One such vesicular carrier system is the niosome. As used herein, the term noisome refers to unilamellar or multilamellar vesicles in which an aqueous phase is encapsulated in highly ordered bilayer made up of nonionic surfactant (Vyas, J. et al., "Development of topical niosomal gel of benzoyl peroxide," International Journal of Nanotechnology, vol. 2011, Article ID 503158, 6 pages, 2011). They are nonionic surfactant vesicles by which skin penetration and accumulation are increased in the superficial skin strata (Manconi, M. et al., Niosomes as carriers for tretinoin: III. A study into the in vitro cutaneous delivery of vesicle-incorporated tretinoin, International Journal of Pharmaceutics, 2006 311 (1-2):11-19); (Vyas, A. et al., Carrier-Based Drug Delivery System for Treatment of Acne, The Scientific World Journal, 2014 Feb. 9; 2014:276260. doi: 10.1155/2014/276260. eCollection 2014.)

The term "synergy" as used herein is intended to refer the interaction of discrete antimicrobial agents in which the total antimicrobial effect is greater than the sum of the effects of the antimicrobial agent alone. Conversely, the term "antagonism" is intended to refer to an interaction of antimicrobial agents in which the total antimicrobial effect is less than the sum of the effects of the antimicrobial agents alone.

The term "checkerboard experimental design", is intended to refer to an in vitro two-dimensional array of serial concentrations of test compounds evaluated in paired or triple combinations for their affect in inhibiting the growth of a target microorganism, measured as a "minimal inhibitory concentration" (MIC), i.e. the lowest concentration that prevents of inhibits microbial growth. It is used as the basis for calculation of a "fractional inhibitory concentration index".

The term "fractional inhibitory concentration index" (FICI) refers to a value that compares the ratio of inhibitory concentration of a combination with that of individual agents separately. The formula used to calculate FICI is as follows:

$$FICI = MICA/B/MICA \text{ alone} + MICB/A/MICB \text{ alone}$$

The FIC Index (FICI) value is used to determine whether paired combinations of antimicrobial agents can exert inhibitory effects against tested organism that are more or less than the sum of their effects alone. In theory, FICI<1.0 indicates synergy and FICI>1.0) indicates antagonism. However, a more conservative calculation has been recommended such that FICI data may be interpreted as "synergy" for an FICI≤0.5, "antagonism" for an FICI>4.0 and "no interaction" interaction for an FICI>0.5-4.0. (Odds, F. C., Synergy, antagonism, and what the chequerboard puts between them, Journal of Antimicrobial Chemotherapy (2003) 52, 1. As used herein, the FICI is interpreted as follows:

$FICI \leq 0.5 = synergy$ $FICI > 0.5 - \leq 1 = additive\ effect$ $FICI > 1 - \leq 4 = indifference$ $FICI > 4 = antagonism$ Unless otherwise indicated, concentrations are given as mass weight percentages, i.e. w/w %. Mass weight percentages (w/w %) for combination formulations are calculated as follows:

$$\text{mass \% } a = \text{mass}(a) \div (\text{mass}(a) + \text{mass}(b) + \text{mass}(c) + \ldots) \times 100\ (w/w\ \%).$$

Compositions

The present invention includes compositions and treatment methods based upon compositions that are combinations of agents having antimicrobial, anti-inflammatory, anti-hyperkeratinization, and anti-commedogenic activities. Such compositions include succinic acid and an API selected from the group consisting of topical retinoids, salicylic acid, azelaic acid, picolinic acid, benzoyl peroxide, antibiotics and combinations thereof.

In various embodiments, the amount of succinic acid in the composition may be from about 0.1 to about 10 w/w % and in particular, from about 0.1, about 0.2, about 0.5 or about 0.75, about 1 w/w % to about 2, about 3, about 4, about 5, about 7.5 or about 10 w/w %. In various embodiments, the amount of succinic acid in the composition may be about 0.1, about 0.2, about 0.5, about 0.75, about 1, about 2, about 3, about 4, about 5, about 6, about 7, about 8, about 9 or about 10 w/w %. The succinic acid is combined with one or more API's.

In various embodiments, salicylic acid may be included in the composition. Salicylic may be present in the composition in an amount of from about 0.05 to about 5 w/w % and in particular, from about 0.05, about 0.1, about 0.2, about 0.5 or about 0.75 w/w % to about 1, about 2, about 3, about 4 or about 5 w/w %. In various embodiments, the amount of salicylic acid in the composition may be about 0.05, about 0.1, about 0.2, about 0.5, about 0.75, about 1, about 2, about 3, about 4 or about 5 w/w %.

In various embodiments, azelaic acid may be included in the composition. Azelaic acid may be present in the composition in an amount of from about 0.05 to about 10 w/w % and in particular, from about 0.05, about 0.1, about 0.2, about 0.5 or about 0.75, about 1 w/w % up to about 2, about 3, about 4, about 5, about 7.5 or about 10 w/w %. In various embodiments, the amount of azelaic acid in the composition may be about 0.05, about 0.1, about 0.2, about 0.5, about 0.75, about 1, about 2, about 3, about 4 about 5, about 7.5 or about 10 w/w %

In various embodiments, picolinic acid may be included in the composition. Picolinic acid may be present in the composition in an amount of from about 0.01 to about 10 w/w % and in particular, from about 0.01, about 0,02, about 0.05, about 0.1, about 0.2 or about 0.5 w/w % to about 0.75, about 1, about 2, about 3, about 4, about 5, about 7.5 or about 10 w/w %. In various embodiments, the amount of picolinic acid in the composition may be about 0.01, about 0.02, about, about 0.05, about 0.1, about 0.2, about 0.5, about 0.75, about 1, about 2, about 3, about 4, about 5, about 7.5 or about 10 w/w %

In various embodiments, benzoyl peroxide may be included in the composition. Benzoyl peroxide may present in the composition in an amount of from about 0.01 to about 5 w/w % and in particular, from about 0.01, about 0,02, about 0.05, about 0.1, about 0.2 or about 0.5 w/w % to about 0.75, about 1, about 2, about 3, about 4 or about 5 w/w %. In various embodiments, the amount of benzoyl peroxide in the composition may be about 0.01, about 0.02, about, about 0.05, about 0.1, about 0.2, about 0.5, about 0.75, about 1, about 2, about 3, about 4 or about 5 w/w %

In various embodiments, antibiotic may be included in the composition. The antibiotic includes erythromycin, clindamycin, minocycline and doxycycline, or any other antibiotic with activity against P. acnes. Antibiotic may be present in the composition in an amount of from about 0.001 up to about 2 w/w % and in particular, from about 0.001, about 0.002, about 0.005 or about 0.0075, about 0.01, about 0.02, about 0.03, about 0.04, about 0.05 w/w % up to about 0.075, about 0.1, about 0.2, about 0.3, about 0.4, about 0.5 about 1 or about 2% w/w %. In various embodiments, the amount of antibiotic in the composition may be about 0.001, about 0.002, about 0.005, about 0.0075, about 0.01, about 0.02, about 0.03, about 0.04, about 0.05, about 0.06, about 0.07, about 0.08, about 0.09, about 0.1, about 0.2, about 0.3, about 0.4, about 0.5, about 1% or about 2 w/w %.

The compositions of the present invention may be incorporated into a pharmaceutically acceptable carrier system which may include creams, gels, lotions or other types of suspensions that can stabilize the combination of agents and deliver them to the affected area of skin by topical applications. Pharmaceutically acceptable carrier systems may also contain ingredients that include, but are not limited to, saline, aqueous electrolyte solutions, ethanol, dimethyl sulfoxide, dimethyl isosorbide, isopropyl myristate, lauryl lactate, diisopropyl adipate, sodium lauryl sulfoacetate; ionic and nonionic osmotic agents such as sodium chloride, potassium chloride, glycerol, propylene glycol and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; compounds such as lecithin, phospholipids; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using preservatives, including, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

Methods of Treatment

The methods of treatment of the present invention are useful for the treatment of skin diseases including acne vulgaris and inflammatory acne vulgaris. Treatment of acne vulgaris may be by topically administering to a subject a composition that includes a combination of active agents.

The compositions of the present invention can be administered at a variety of intervals. In some instances, administration may be once a day. In other instances, administration can be less or more frequently, such as 1, 2, 3, or 4 times a day, 1 time every 2 days, or once a week.

The treatment methods may be monitored by following any of the pathogenic aspects of acne vulgaris including number of acne lesions, sebum excretion, follicular keratinization, comedone formation, bacterial colonization of the follicle, *P. acnes* proliferation and/or inflammation.

EXAMPLES

Aspects of the present teachings may be further understood in light of the following examples, which should not be construed as limiting the scope of the present teachings in any way. In the examples below, DRM1 refers to succinic acid.

Example 1—this Example Illustrates the Antimicrobial Effect of Combinations of DRM1 (Succinic Acid) and Salicylic Acid Using a Checkerboard Assay Design Bacterial Cultivation

*P. acnes* (ATCC 6919) was cultured on *Brucella* plates supplemented with 0.1 g/L hemin, 0.01 g/L vitamin K, and 5% (v/v) defibrinated sheep's blood at 37° C. under anaerobic conditions using a Gas-Pak (BD). For each assay, an inoculum of *P. acnes* was prepared by suspending a colony of *P. acnes* in 5 mL Reinforced *Clostridium* medium (RCM) and growing at 37° C. and 250 RPM under anaerobic conditions for 30 hours. Cultures were harvested, washed with PBS and resuspended in fresh, sterile RCM broth to a concentration of 2×106 CFU/ml.

Minimum Inhibitory Concentration (MIC) Determination

Individual MIC values were determined for each drug according to the microbroth dilution method. Briefly, 2-fold serial dilutions of each drug (50 µl) were added to wells in a 96-well plate followed by 50 µl of the prepared *P. acnes* inoculum as described in Example 1. Media without *P. acnes* and medium with *P. acnes* only were used for negative and positive controls, respectively, and contained the highest concentration of solvent used in each drug analysis. Plates were incubated under anaerobic conditions using a Gas-Pak (BD) for 48 hours at 37° C. Following incubation, each well was resuspended by pipetting and the optical density at 600 nm (OD600) was determined on a plate reader. The MIC value was defined as the first well showing >90% reduction in growth compared to controls.

In vitro Checkerboard Assay

A checkerboard assay was used to determine if combining DRM1 (succinic acid) with commonly used topical treatments for acne showed synergy, indifference or antagonism between the drugs. Checkerboard assays were performed in 96 well plates as an 8×8 grid. Two-fold serial dilutions of API A (25 µl) were added at 4× the desired final concentration across 8 rows of the microplate. Two-fold serial dilutions of API B (25 µl) were added at 4× the desired final concentration to 8 columns on the microplate so that the highest concentration of API A and the highest concentration of API B were in the same well at one corner of the 8×8 grid diagonal from the corner containing the lowest concentration of each drug. For each drug, a set of concentrations greater than and less than the MIC as calculated above was used. An inoculum of *P. acnes* (50 µl) as described in example 1 was added to each well containing API and the plate was incubated at 37° C. for 48 hours under anaerobic conditions and the individual and combined MIC values were determined as stated in example 2 for the MIC assay. The FICI for each combination was determined using the following equation:

$$FICI = MICA_B/MICA\ alone + MICB_A/MICB\ alone$$

Synergy was defined as an FICI≤0.5, additivity was defined as an FICI >0.5≤1.0, indifference was defined as an FICI >1≤4 and antagonism was defined as an FICI>4.0.

Checkerboard Combination of DRM1 (Succinic Acid) and Salicylic Acid

Table 1, below, shows the MIC values for Salicylic Acid.

Figure 2:
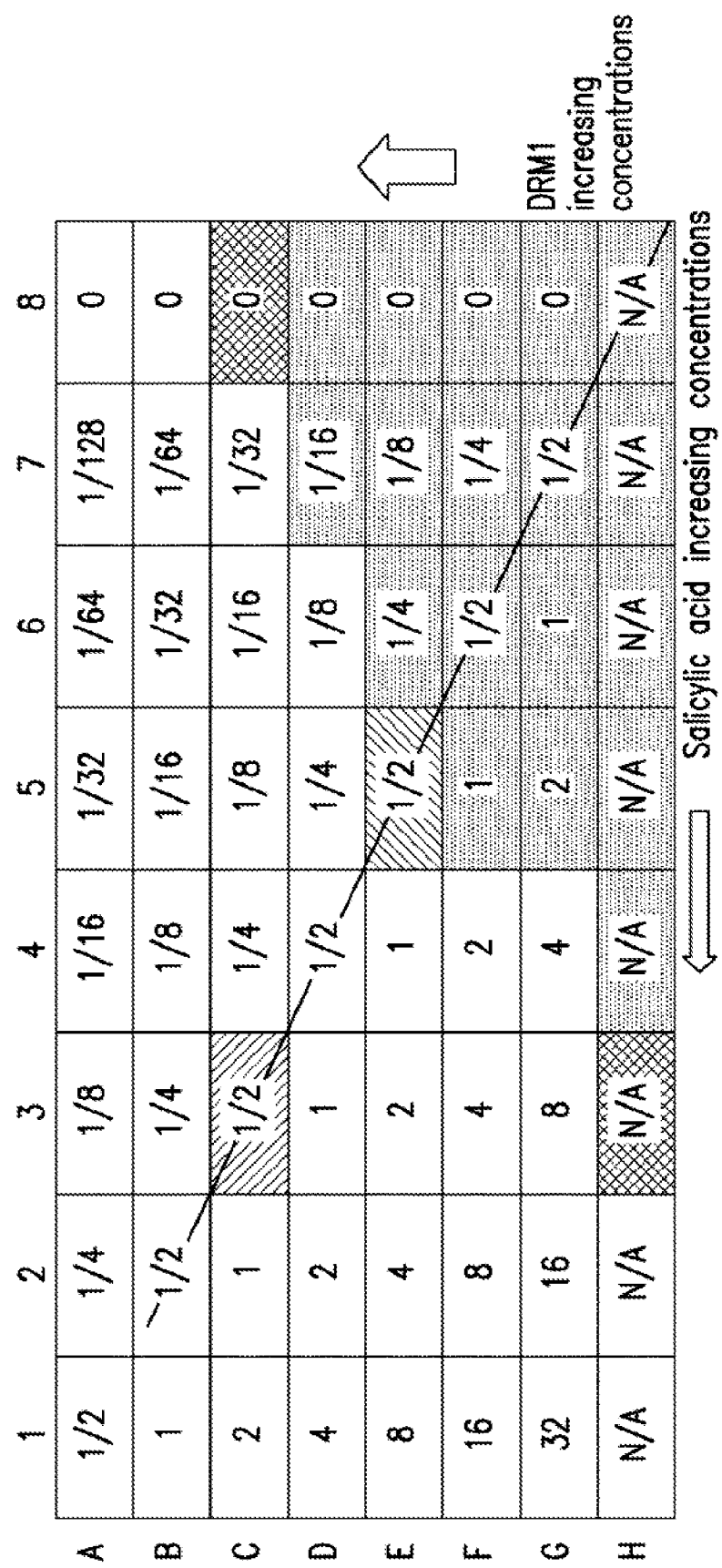

As shown in FIGS. 1 and 2 and Table 1, the combined MIC of the two drugs was found to be 3.75 mM DRM1 (succinic acid) and 1.9 mM salicylic acid as seen in FIG. 1. This corresponded to an FICI of 0.5 suggesting synergy was occurring between DRM1 (succinic acid) and salicylic acid. Growth inhibition was seen when salicylic acid and DRM1 (succinic acid) were used at a ratio of 1:32 when the concentration of DRM1 (succinic acid) was ≥15 mM and the concentration of salicylic acid was ≥0.47 mM, when salicylic acid and DRM1 (succinic acid) were used in a ratio of 1:8 when the concentration of DRM1 (succinic acid) was ≥7.5 mM and the concentration of salicylic acid was ≥0.94 mM, when salicylic acid and DRM1 (succinic acid) were used in a ratio of 1:2 when the concentration of DRM1 (succinic acid) was ≥3.75 mM and the concentration of salicylic acid was ≥1.9 mM, when salicylic acid and DRM1 (succinic acid) were used in a ratio of 2:1 when the concentration of DRM1 (succinic acid) was ≥1.9 and the concentration of salicylic acid was ≥3.75 mM, and when salicylic acid and DRM1 (succinic acid) were used in a ratio of 4:1 when the concentration of DRM1 (succinic acid) was ≥0.94 mM and the concentration of salicylic acid was ≥3.75 mM as seen in FIG. 2. Using the control *P. acnes* strain, ATCC 6919, DRM1 (succinic acid) in combination with SA resulted in an FICI of 0.5 suggesting the two active pharmaceutical ingredients (APIs) are working in synergy. The most synergistic concentration of the two APIs occurred at a ratio of 2:1 (DRM1:SA) when DRM1 (succinic acid) (3.75 mM) was combined with SA (1.9 mM), at a quarter of the MIC concentration required for each component alone. (See Table 1 below)

TABLE 1

MIC's for Salicylic Acid in combination with Succinic Acid

| Salicylic Acid (mM) | DRM1 (Succinic Acid mM) | Ratio (Salicylic/DRM1) | FICI | Synergistic/ Additive/Indifferent/ Antagonist |
|---|---|---|---|---|
| 0 | 15 | — | — | — |
| 7.5 | 0 | — | — | — |
| 1.9 | 3.75 | 1:2 | 1.9/7.5 + 3.75/15 = 0.5 | Synergistic |
| ≥0.47 | ≥15 | 1:32 | ≥0.47/7.5 + ≥15/15 = ≥1.06 | Additive |
| ≥0.94 | ≥7.5 | 1:8 | ≥0.94/7.5 + ≥7.5/15 = ≥0.625 | Additive |
| ≥1.9 | ≥3.75 | 1:2 | ≥1.9/7.5 + ≥3.75/15 = ≥0.5 | Synergistic |
| ≥3.75 | ≥1.9 | 2:1 | ≥3.75/7.5 + ≥1.9/15 = ≥0.626 | Additive |
| ≥3.75 | ≥0.94 | 4:1 | ≥3.75/7.5 + ≥0.94/15 = ≥0.563 | Additive |

Figure 3:
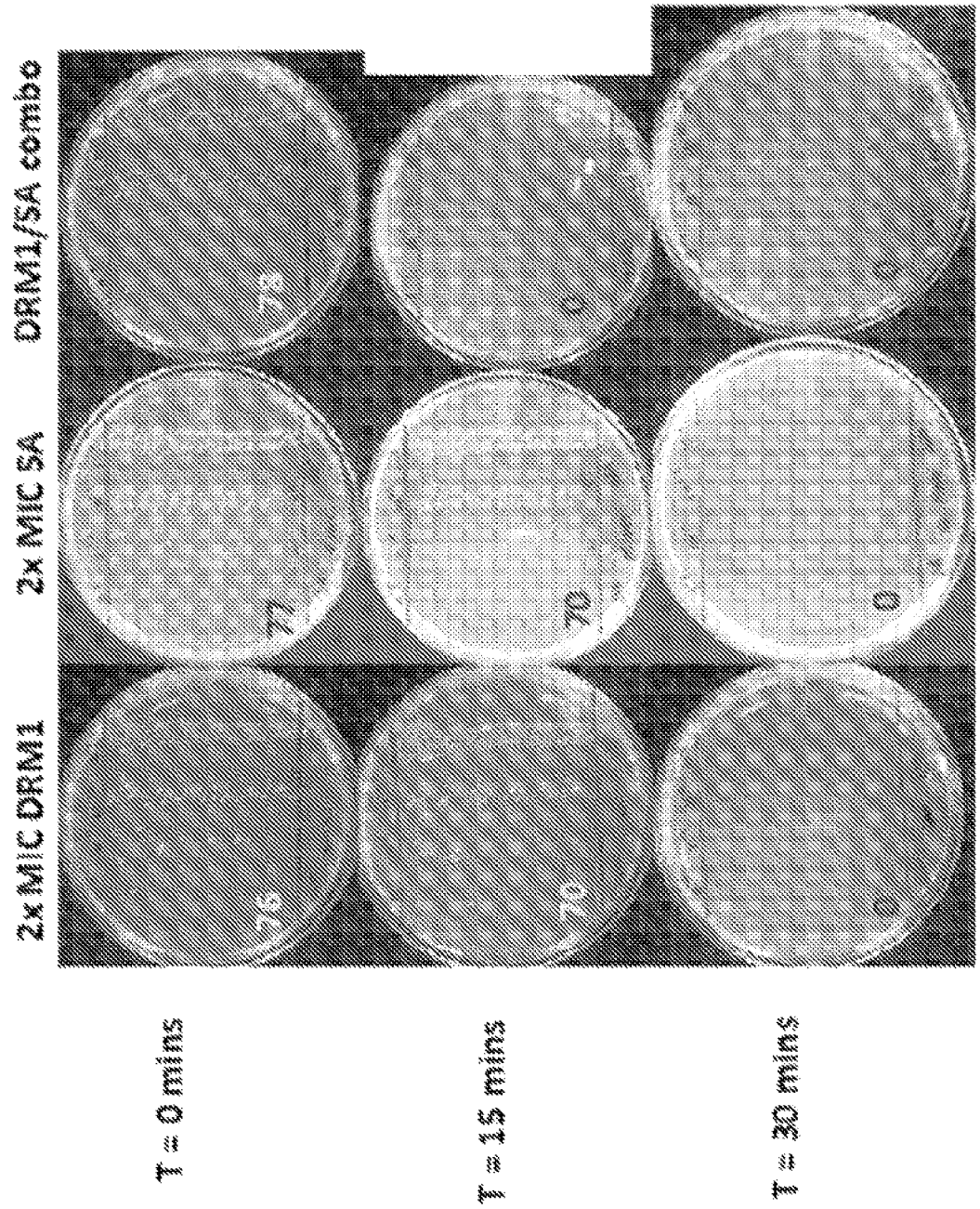

Example 2—this Example Illustrates the Time-Kill Assay of DRM1 (Succinic Acid) and Salicylic Acid in Combination DRM1 (succinic acid) and salicylic acid were used individually at concentrations 2× their MIC values (30 mM DRM1 (succinic acid) and 15 mM salicylic acid) and in combination at 0.5× MIC for DRM1 (succinic acid, 7.5 mM) and 1× MIC for salicylic acid (7.5 mM) Assays were performed in RCM broth with 12% propylene glycol in 96-well plates. A final concentration of 5×10⁵ CFU/ml $P.$ $acnes$ 6919 was used for each reaction and each assay was performed under anaerobic conditions using a Gas-Pak at 37° C. At various time points (0, 15, 30, 60 and 120 minutes) 10 μl of each sample was removed and diluted 1:10 to 1:10⁴ in sterile PBS and 20 μl of each dilution was spread on a $Brucella$ broth agar plate supplemented with 0.1 μg/ml hemin and 0.01 μg/ml vitamin K using the track plate method. FIG. 3 shows a consistent growth between all three samples and the control at 0 minutes. After 15 minutes, growth was evident on the individual DRM1 (succinic acid) and salicylic acid plates; however, no growth was detected on the DRM1 (succinic acid)-salicylic acid combination plate. After 30 minutes of incubation, no growth was detected on any of the plates. The increased speed at which the DRM1 (succinic acid)-salicylic acid combination inhibited $P.$ $acnes$ growth suggests the two APIs performed in a synergistic or additive way.

Example 3—this Example Illustrates the Antimicrobial Effect of Combinations of DRM1 (Succinic Acid) and Azelaic Acid Using a Checkerboard Assay Design Bacterial cultivation, MIC calculation and Checkerboard Assay design were as described in Example 1. Table 2, below, shows MIC values for Azelaic Acid.

Figure 4:
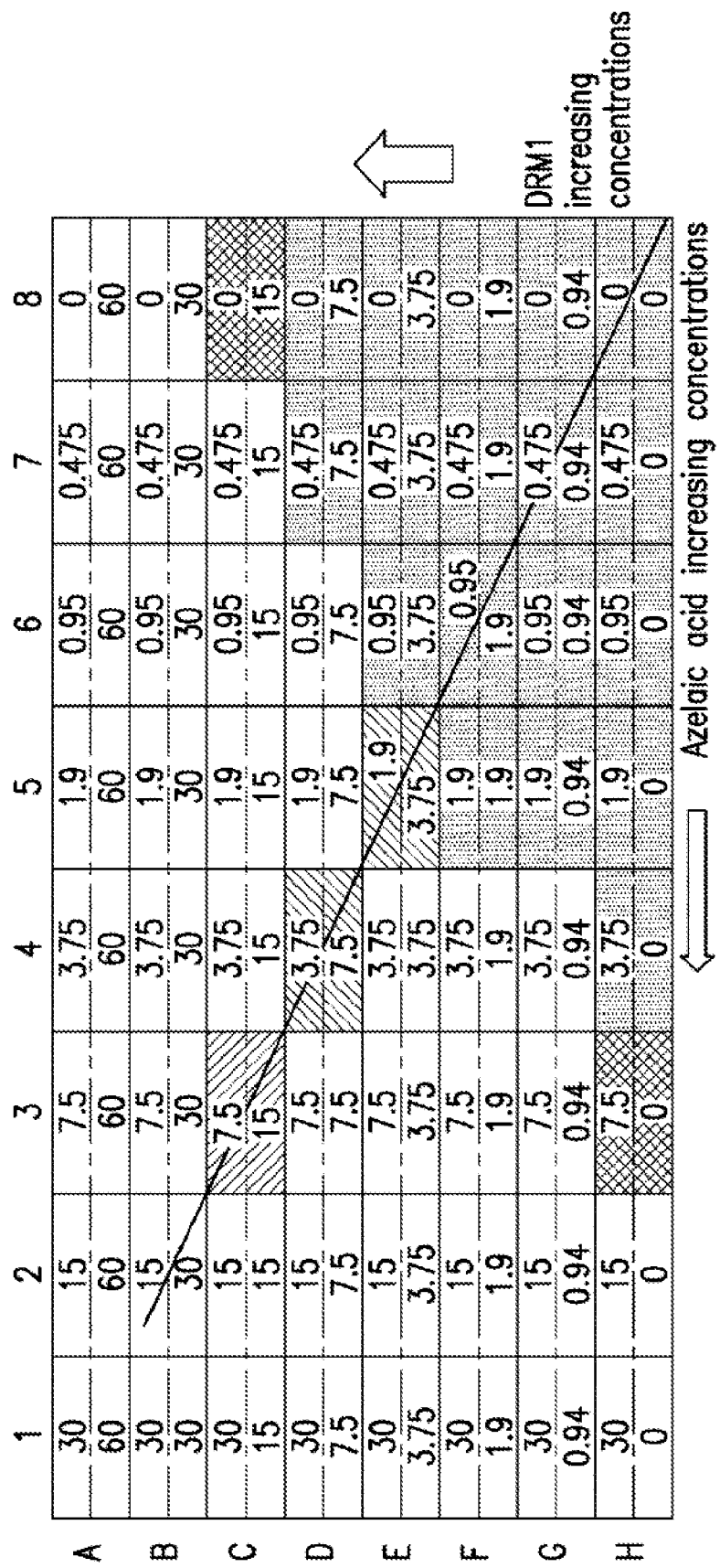
Figure 5:
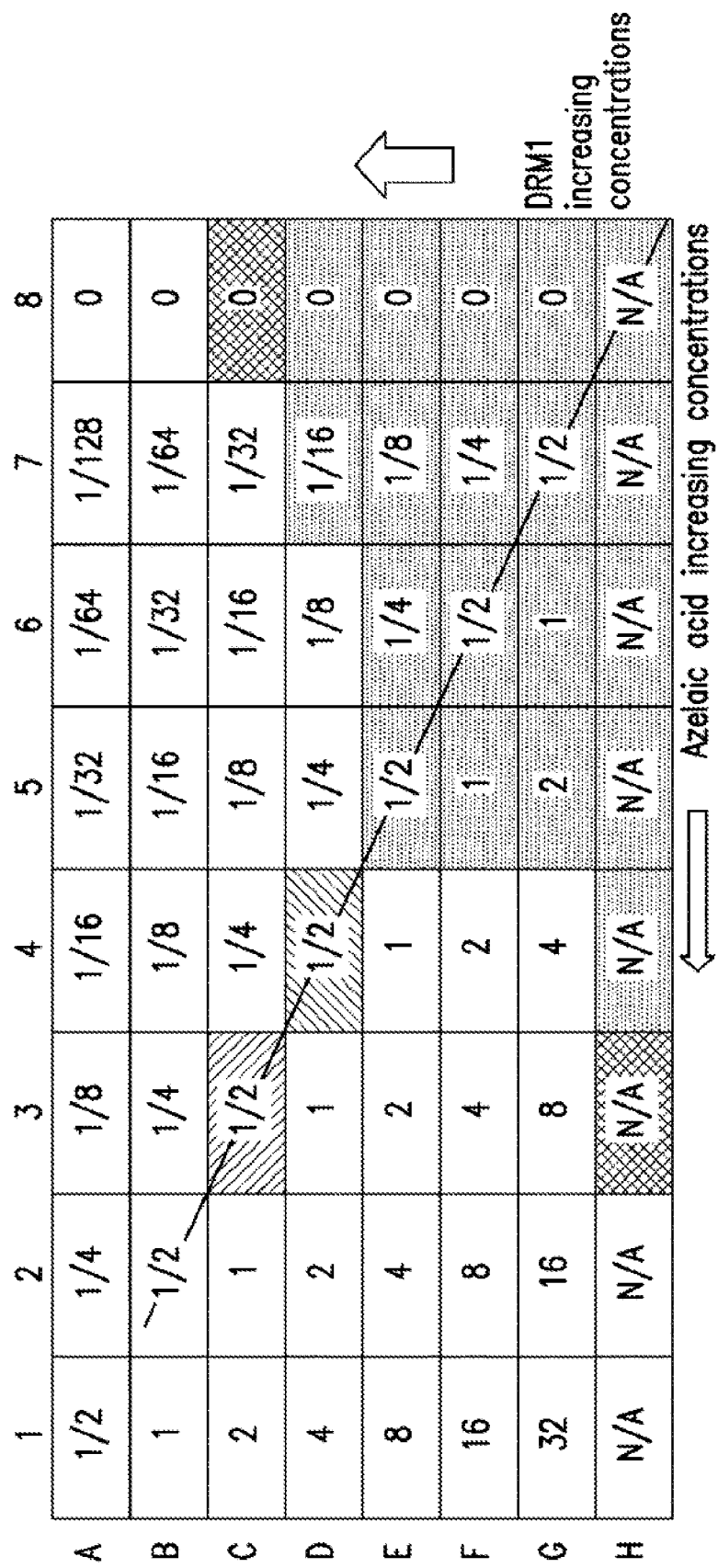

As shown in FIGS. 4 and 5 and Table 2, the combined MIC of the two drugs was at 7.5 mM DRM1 (succinic acid) and 3.75 mM azelaic acid as seen in FIG. 4. This corresponded to an FICI of 1.0 suggesting the interaction between DRM1 (succinic acid) and azelaic acid was additive. Growth inhibition was seen when azelaic acid and DRM1 (succinic acid) were used at a ratio 1:32 when the concentration of DRM1 (succinic acid) was ≥15 mM and the concentration of azelaic acid was ≥0.47 mM, when azelaic acid and DRM1 (succinic acid) were used in a ratio of 1:8 when the concentration of DRM1 (succinic acid) was ≥7.5 mM and the concentration of azelaic acid was ≥0.94 mM, when azelaic acid and DRM1 (succinic acid) were used in a ratio of 1:4 when the concentration of DRM1 (succinic acid) was ≥7.5 mM and the concentration of azelaic acid was ≥1.9 mM, when azelaic acid and DRM1 (succinic acid) were used in a ratio of 1:2 when the concentration of DRM1 (succinic acid) was ≥7.5 mM and the concentration of azelaic acid was ≥3.75 mM, when azelaic acid and DRM1 (succinic acid) were used in a ratio of 1:1 when the concentration of DRM1 (succinic acid) was ≥3.75 and the concentration of azelaic acid was ≥3.75 mM, when azelaic acid and DRM1 (succinic acid) were used in a ratio of 2:1 when the concentration of DRM1 (succinic acid) was ≥1.9 mM and the concentration of azelaic acid was ≥3.75 mM, and when azelaic acid and DRM1 (succinic acid) were used in a ratio of 8:1 when the concentration of DRM1 (succinic acid) was ≥0.94 mM and the concentration of azelaic acid was ≥7.5 mM as seen in FIG. 5. DRM1 (succinic acid) in combination with AZA had additive effect and killed $P.$ $acnes$ at half the concentration each when used in combination. The concentration of AZA can be lowered which results in less side effect while maintaining efficacy of the combination.

TABLE 2

MIC's for Azelaic Acid in combination with Succinic Acid

| Azelaic acid (mM) | DRM1 (Succinic Acid mM) | Ratio (Azelaic/DRM1) | FICI | Synergistic/ Additive/Indifferent/ Antagonist |
|---|---|---|---|---|
| 0 | 15 | — | — | — |
| 7.5 | 0 | — | — | — |
| 3.75 | 7.5 | 1:2 | 3.75/7.5 + 7.5/15 = 1.0 | Additive |
| ≥0.47 | ≥15 | 1:32 | ≥0.47/7.5 + ≥15/15 = ≥1.06 | Indifferent |
| ≥0.94 | ≥7.5 | 1:8 | ≥0.94/7.5 + ≥7.5/15 = ≥0.625 | Additive |
| ≥1.9 | ≥7.5 | 1:4 | ≥1.9/7.5 + ≥7.5/15 = ≥0.75 | Additive |
| ≥3.75 | ≥7.5 | 1:2 | ≥3.75/7.5 + ≥7.5/15 = ≥1.0 | Additive |
| ≥3.75 | ≥3.75 | 1:1 | ≥3.75/7.5 + ≥3.75/15 = ≥0.75 | Additive |

TABLE 2-continued

MIC's for Azelaic Acid in combination with Succinic Acid

| Azelaic acid (mM) | DRM1 (Succinic Acid mM) | Ratio (Azelaic/DRM1) | FICI | Synergistic/ Additive/Indifferent/ Antagonist |
|---|---|---|---|---|
| ≥3.75 | ≥1.9 | 2:1 | ≥3.75/7.5 + ≥1.9/15 = ≥0.63 | Additive |
| ≥7.5 | ≥0.94 | 8:1 | ≥7.5/7.5 + ≥0.94/15 = ≥1.06 | Indifferent |

Example 4—this Example Illustrates the Antimicrobial Effect of Combinations of DRM1 (Succinic Acid) and Picolinic Acid Using a Checkerboard Assay Design Bacterial cultivation, MIC calculation and Checkerboard Assay design were as described in Example 1. Table 3, below, shows MIC values for picolinic acid.

Figure 6:
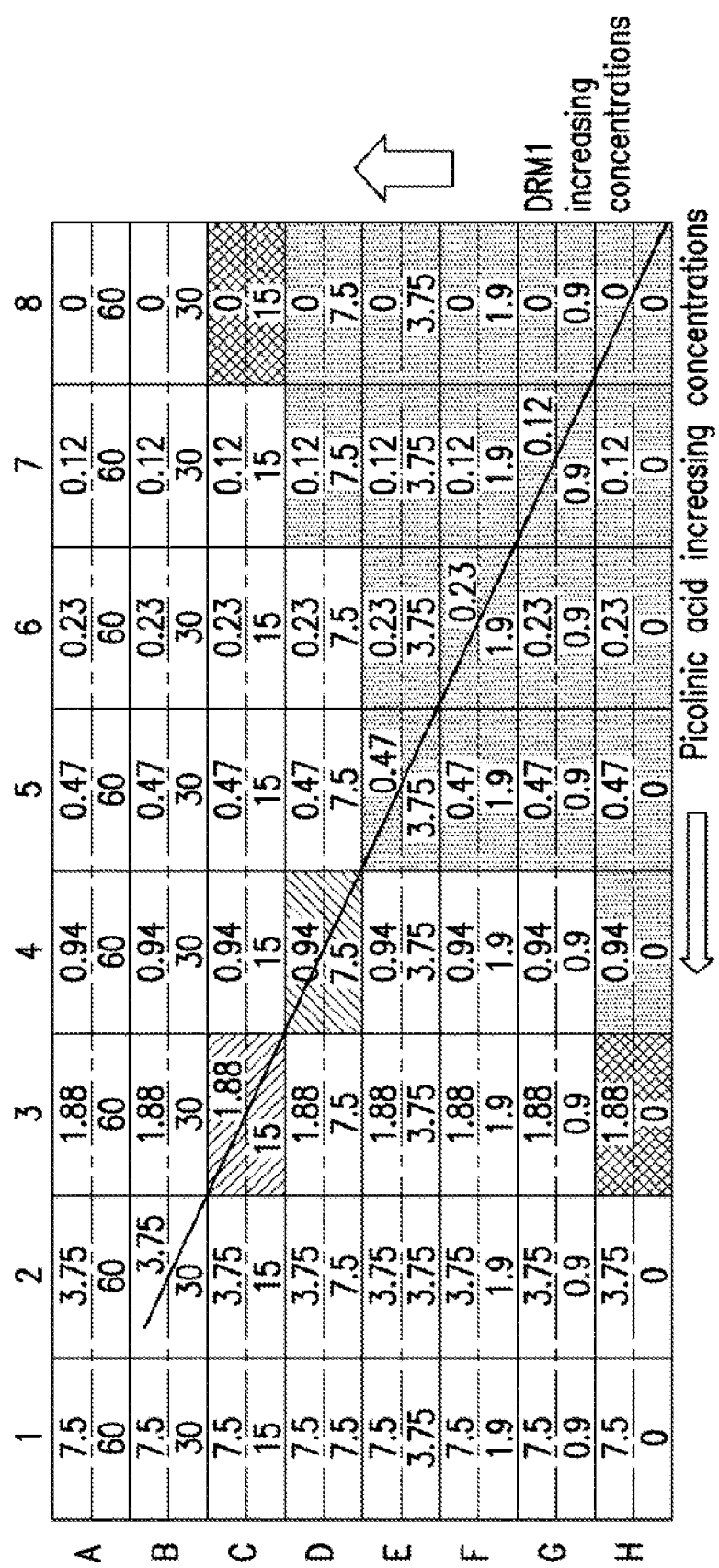

As shown in FIGS. 6 and 7 and Table 3, DRM1 (succinic acid, 0-60 mM) and picolinic acid (0-7.5 mM) were added to a 96-well plate in 2-fold serial dilutions and combined with *P. acnes* 6919 as described in example 1. The combined MIC of the two drugs was at 7.5 mM DRM1 (succinic acid) and 0.94 mM picolinic acid as seen in FIG. 6. This corresponded to an FICI of 1.0 suggesting the interaction between DRM1 (succinic acid) and picolinic acid was additive. Growth inhibition was seen when picolinic acid and DRM1 (succinic acid) were used at a ratio 1:128 when the concentration of DRM1 (succinic acid) was ≥15 mM and the concentration of picolinic acid was ≥0.12 mM, when picolinic acid and DRM1 (succinic acid) were used in a ratio of 1:64 when the concentration of DRM1 (succinic acid) was ≥15 mM and the concentration of picolinic acid was ≥0.23 mM, when picolinic acid and DRM1 (succinic acid) were used in a ratio of 1:16 when the concentration of DRM1 (succinic acid) was ≥7.5 mM and the concentration of picolinic acid was ≥0.47 mM, when picolinic acid and DRM1 (succinic acid) were used in a ratio of 1:8 when the of DRM1 (succinic acid) was ≥7.5 mM and the concentration of picolinic acid was ≥0.94 mM, when picolinic acid and DRM1 (succinic acid) were used in a ratio of 1:4 when the concentration of DRM1 (succinic acid) was ≥3.75 mM and the concentration of picolinic acid was ≥0.94 mM, when picolinic acid and DRM1 (succinic acid) were used in a ratio of 1:2 when the concentration of DRM1 (succinic acid) was ≥3.75 mM and the concentration of picolinic acid was ≥1.88 mM, when picolinic acid and DRM1 (succinic acid) were used in a ratio of 1:1 when the concentration of DRM1 (succinic acid) was ≥1.9 mM and the concentration of picolinic acid was ≥1.9 mM and when picolinic acid and DRM1 (succinic acid) were used in a ratio of 2:1 when the concentration of DRM1 (succinic acid) was ≥0.9 mM and the concentration of picolinic acid was ≥1.88 mM as seen in FIG. 7. DRM1 (succinic acid) in combination with picolinic acid had additive effect and killed *P. acnes* at half the concentration each when used in combination. The concentration of picolinic acid can be lowered which results in less side effect while maintaining efficacy of the combination.

TABLE 3

MIC's for Picolinic Acid in combination with Succinic Acid

| Picolinic acid (mM) | DRM1 (Succinic Acid mM) | Ratio (Picolinic/ DRM1) | FICI | Synergistic/ Additive/Indifferent/ Antagonist |
|---|---|---|---|---|
| 0 | 15 | — | — | — |
| 1.88 | 0 | — | — | — |
| 0.94 | 7.5 | 1:8 | 0.94/1.88 + 7.5/15 = 1.0 | Additive |
| ≥0.12 | ≥15 | 1:128 | ≥0.12/1.88 + ≥15/15 = ≥1.06 | Indifferent |
| ≥0.23 | ≥15 | 1:64 | ≥0.23/1.88 + ≥15/15 = ≥1.12 | Indifferent |
| ≥0.47 | ≥7.5 | 1:16 | ≥0.47/1.88 + ≥7.5/15 = ≥0.75 | Additive |
| ≥0.94 | ≥7.5 | 1:8 | ≥0.94/1.88 + ≥7.5/15 = ≥1.0 | Additive |
| ≥0.94 | ≥3.75 | 1:4 | ≥0.94/1.88 + ≥3.75/15 = ≥0.75 | Additive |
| ≥1.88 | ≥3.75 | 1:2 | ≥1.88/1.88 + ≥3.75/15 = 1.25 | Indifferent |
| ≥1.88 | ≥1.9 | 1:1 | ≥1.88/1.88 + ≥1.9/15 = ≥1.13 | Indifferent |
| ≥1.88 | ≥0.9 | 2:1 | ≥1.88/1.88 + ≥0.9/15 = ≥1.06 | Indifferent |

Example 5—this Example Illustrates the Antimicrobial Effect of Combinations of DRM1 (Succinic Acid) and Benzoyl Peroxide (BPO) Using a Checkerboard Assay Design Bacterial cultivation, MIC calculation and Checkerboard Assay design were as described in Example 1. Table 4, below shows MIC values for BPO.

Figure 9:
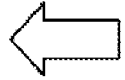

As shown in FIGS. 8 and 9 and Table 4, DRM1 (succinic acid, 0-7085 µg/ml) and benzoyl peroxide (0-250 µg/ml) were added to a 96-well plate in 2-fold serial dilutions and combined with *P. acnes* 6919 as described in example 3. DRM1 (succinic acid) had an individual MIC value of 1771 µg/ml and BPO had an individual MIC (succinic acid) value of 125 µg/ml. The combined MIC of the two drugs was at 885.7 µg/ml DRM1 (succinic acid) and 62.5 µg/ml BPO as seen in FIG. 8. This corresponded to an FICI of 1.0 suggesting the interaction between DRM1 (succinic acid) and BPO was additive. Growth inhibition was seen when BPO and DRM1 (succinic acid) were used at ratios of 1:113, 1:226, and 1:453 when DRM1 (succinic acid) was used at a concentration ≥1771 µg/ml and BPO was used at a concentration ≥15.6 µg/ml, ≥7.8 µg/ml, and ≥3.9 µg/ml, respectively, as seen in FIG. 9. Growth inhibition was also seen at a ratio of BPO to DRM1 (succinic acid) of about 1:14 and 1:28 when the concentration of DRM1 (succinic acid) was ≥885.7 µg/ml and BPO was used at ≥62.5 µg/ml, and ≥31.25

µg/ml, respectively, or when the ratio of BPO to DRM1 (succinic acid) was about 1:7, 1:3.5, 1:1.8, or 1:0.88 at concentrations of BPO≥125 µg/ml and concentrations of DRM1 (succinic acid) at ≥885.7 µg/ml, ≥442 µg/ml, ≥221 µg/ml, and ≥110 µg/ml, respectively. DRM1 (succinic acid) in combination with BPO had additive effect and killed *P. acnes* at half the concentration each when used in combination. The concentration of BPO can be lowered which results in less side effect while maintaining efficacy of the combination.

TABLE 4

MIC's for Benzoyl Peroxide (BPO) in combination with Succinic Acid

| BPO (µg/ml) | DRM1 (Succinic Acid µg/ml) | Ratio (BPO/DRM1) | FICI | Synergistic/ Additive/Indifferent/ Antagonist |
|---|---|---|---|---|
| 0 | 1771 | — | — | — |
| 125 | 0 | — | — | — |
| 62.5 | 885.7 | 1:14 | 62.5/125 + 885.7/1771 = 1.0 | Additive |
| ≥3.9 | ≥1771 | 1:453 | ≥3.9/125 + ≥1771/1771 = ≥1.03 | Indifferent |
| ≥7.8 | ≥1771 | 1:226 | ≥7.8/125 + ≥1771/1771 = ≥1.06 | Indifferent |
| ≥15.6 | ≥1771 | 1:113, | ≥15.6/125 + ≥1771/1771 = ≥1.12 | Indifferent |
| ≥31.25 | ≥885.7 | 1:28 | ≥31.25/125 + ≥885.7/1771 = ≥0.75 | Additive |
| ≥62.5 | ≥885.7 | 1:14 | ≥62.5/125 + ≥885.7/1771 = ≥1.0 | -Additive- |
| ≥125 | ≥885.7 | 1:7 | ≥125/125 + ≥885.7/1771 = ≥1.5 | Indifferent |
| ≥125 | ≥442 | 1:3.5 | ≥125/125 + ≥442/1771 = 1.25 | Indifferent |
| ≥125 | ≥221 | 1:1.8 | ≥125/125 + ≥221/1771 = ≥1.12 | Indifferent |
| ≥125 | ≥110 | 1:0.88 | ≥125/125 + ≥≥110/1771 = ≥1.06 | Indifferent |

Discussion of Examples: 1-5

Examples 1-5 Illustrate DRM1 (Succinic Acid) Combinations that Maximize Efficacy and Minimize Side Effects DRM1 (succinic acid) increases efficacy of other acne treatments including salicylic acid, benzoyl peroxide, azelaic acid, picolinic acid, retinoids, etc. while reducing side effects of the second agents on the skin. This means that combinations can be used in which the amount of a side effect causing agent (such as benzoyl peroxide (BPO), salicylic acid, azelaic acid, retinoids, etc.) can be reduced while maximizing efficacy. We have identified DRM1 (succinic acid) containing combinations and the ratios between DRM1 (succinic acid) and the second agent that are optimal for acne treatment. All combinations improve the performance of the second agent without increasing side effects—they reduce side effects). The most efficacious combination seems to be DRM1 (succinic acid)+salicylic acid at ratio 2:1. This combination shows the highest synergistic effects against *P. acnes*, reduces inflammation (provided by DRM1), and has anti-hyperkeratinization (provided by salicylic acid) and anti-commedogenic (provided by salicylic acid) properties. This combination addresses three acne vulgaris diseases factors. In addition, the combinations result in faster killing of *P. acnes* (time kill assays in Example 2) and prevents biofilm formation in DRM1 concentration above 7.5 mM (Example 8). The combinations of DRM1 (succinic acid) with a second agent can be optimized using specific molar ratios to achieve optimal efficacy while minimizing side effects. In addition to treating acne vulgaris in all patients including inflammatory acne vulgaris, DRM1 (succinic acid) containing combinations could be particularly useful in patients who are prone to side effects on the skin and would benefit from suing topical treatments that contain reduced amount of BPO, salicylic acid, azelaic acid, retinoids, etc.

Example 6—this Example Illustrates the Antimicrobial Effect of Combinations of DRM1 (Succinic Acid) and Clindamycin Using a Checkerboard Assay Design Bacterial cultivation, MIC calculation and Checkerboard Assay design were as described in Example 1. Table 5, below, shows MIC values for BPO.

Figure 10:
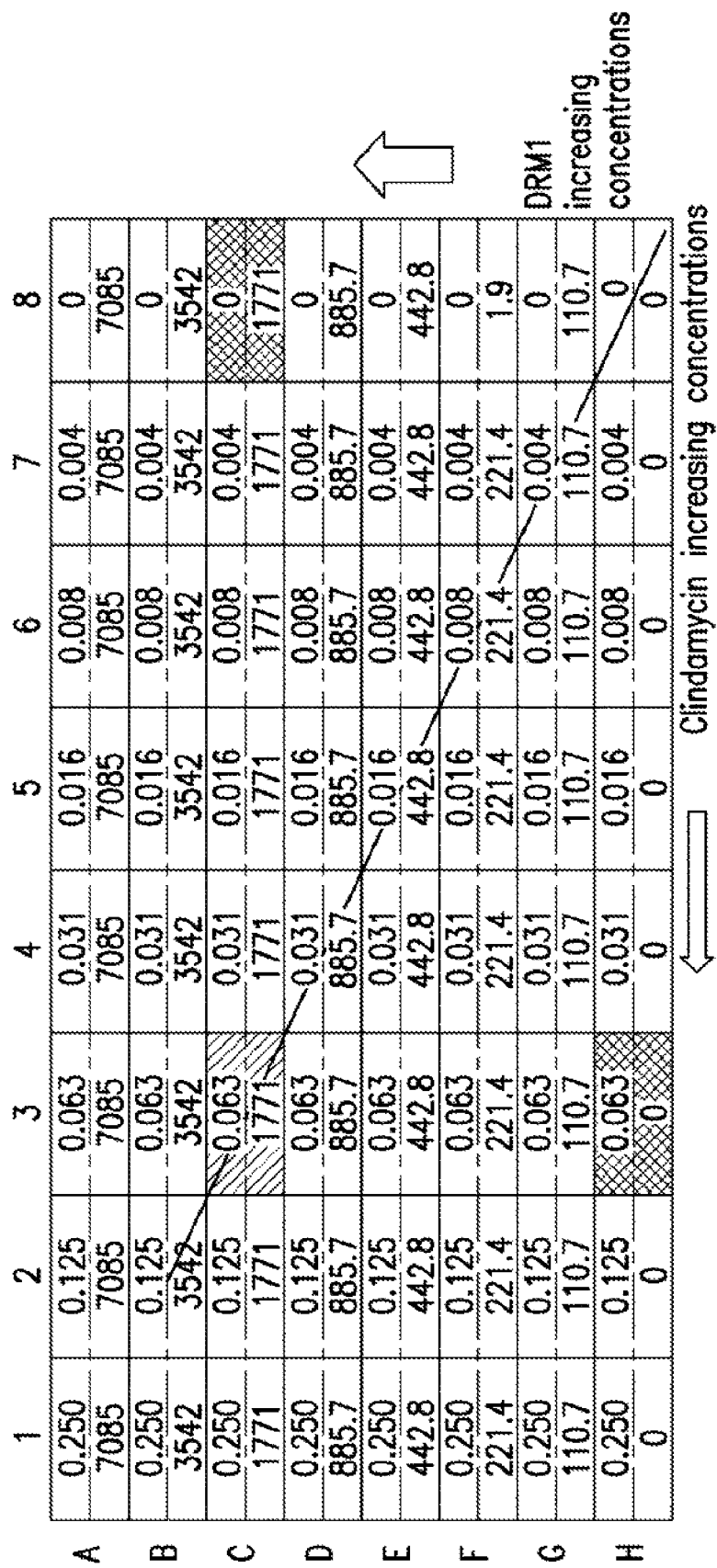
Figure 11:
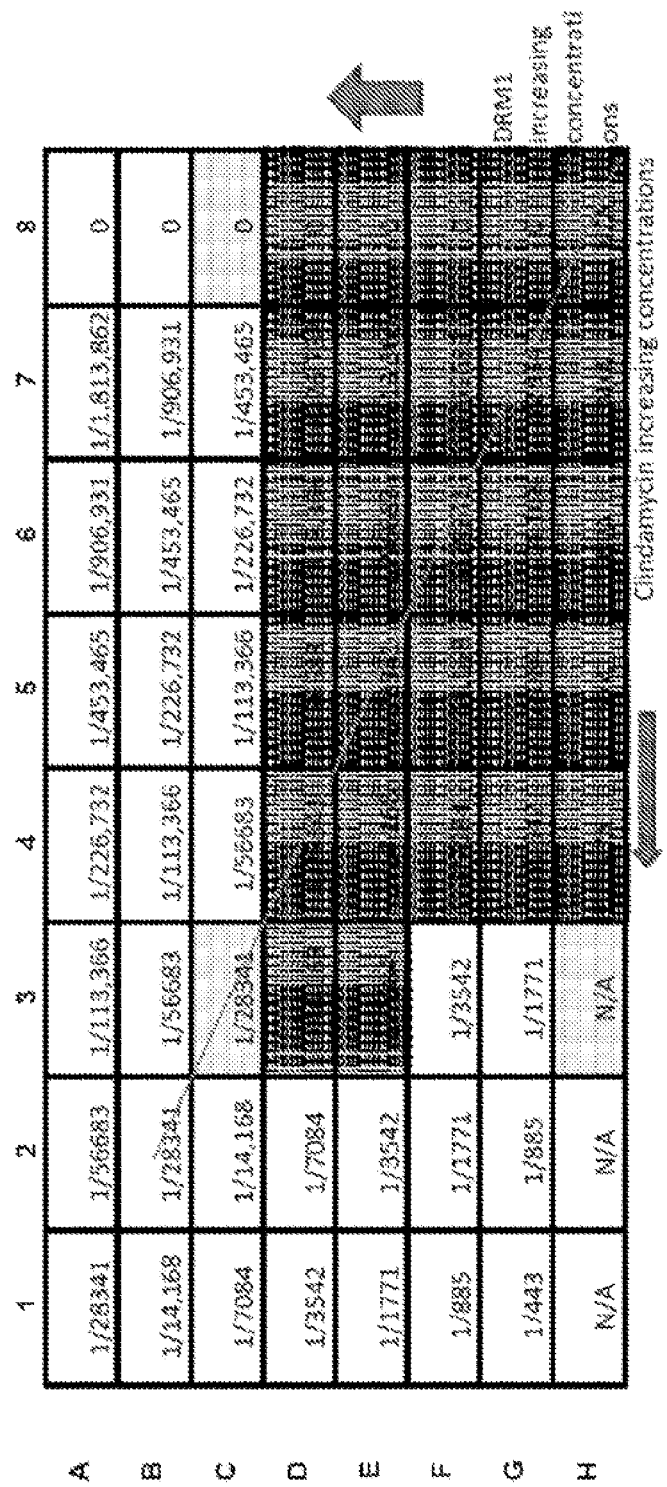

As shown in FIGS. 10 and 11 and Table 5, DRM1 (succinic acid, 0-7085 µg/ml) and clindamycin (0-0.25 µg/ml) were added to a 96-well plate in 2-fold serial dilutions and combined with *P. acnes* 6919 as described in example 3. The combined MIC of the two drugs was at 1771 µg/ml DRM1 (succinic acid) and 0.06 µg/ml clindamycin, which were the same MIC values for each individual treatment as seen in FIG. 10. This corresponded to an FICI of 2.0 suggesting the interaction between DRM1 (succinic acid) and clindamycin was indifferent with no indication of an antagonistic interaction. Growth inhibition was seen when clindamycin and DRM1 (succinic acid) were used at ratios of 1:28341, 1:56683, 1:113366, 1:226732, 1:453465 when DRM1 (succinic acid) was used at a concentration ≥1771 µg/ml and clindamycin was used at a concentration ≥0.063 µg/ml, ≥0.031 µg/ml, ≥0.016 µg/ml, ≥0.008 µg/ml, and ≥0.004 µg/ml, respectively, as seen in FIG. 11.

TABLE 5

MIC's for Clindamycin in combination with Succinic Acid

| Clindamycin (μg/ml) | DRM1 (Succinic Acid μg/ml) | Ratio (Clindamycin/ DRM1) | FICI | Synergistic/ Additive/Indifferent/ Antagonist |
|---|---|---|---|---|
| 0 | 1771 | — | — | — |
| 0.063 | 0 | — | — | — |
| 0.063 | 1771 | 1:28341 | 0.063/0.063 + 885.7/1771 = 2.0 | Indifferent |
| ≥0.004 | ≥1771 | 1:453465 | ≥0.004/0.063 + ≥1771/1771 = ≥1.07 | Indifferent |
| ≥0.008 | ≥1771 | 1:226732, | ≥0.008/0.063 + ≥1771/1771 = ≥1.13 | Indifferent |
| ≥0.016 | ≥1771 | 1:113366 | ≥0.016/0.063 + ≥1771/1771 = ≥1.27 | Indifferent |
| ≥0.031 | ≥1771 | 1:56683, | ≥0.031/0.063 + ≥885.7/1771 = ≥1.52 | Indifferent |
| ≥0.063 | ≥1771 | 1:28341 | ≥0.063/0.063 + ≥885.7/1771 = ≥2.05 | Indifferent |
| ≥0.063 | ≥221.4 | 1:3514 | ≥0.063/0.063 + ≥221.4/1771 = ≥1.17 | Indifferent |
| ≥0.063 | ≥110.7 | 1:1757 | ≥0.063/0.063 + ≥110.7/1771 = ≥1.11 | Indifferent |

Table 6 summarizes the MIC values from Examples 1, 3, 4, 5 and 6.

TABLE 6

Summary of MIC values

| API | API Conc. | DRM1 Conc. (Succinic Acid) | Ratio (API/ DRM1) | FICI | Synergistic/ Additive/Indifferent/ Antagonist |
|---|---|---|---|---|---|
| Salicylic Acid | 1.9 mM | 3.75 mM | 1:2 | 1.9/7.5 + 3.75/15 = 0.5 | Synergistic |
| Azelaic acid | 3.75 mM | 7.5 mM | 1:2 | 3.75/7.5 + 7.5/15 = 1.0 | Additive |
| Picolinic Acid | 0.94 mM | 7.5 mM | 1:8 | 0.94/1.88 + 7.5/15 = 1.0 | Additive |
| Benzoyl Peroxide | 62.5 μg/ml | 885.7 μg/ml | 1:14 | 62.5/125 + 885.7/1771 = 1.0 | Additive |
| Clindamycin | 0.063 μg/ml | 1771 μg/ml | 1:28341 | 0.063/0.063 + 885.7/1771 = 2.0 | Indifferent |

Figure 12:
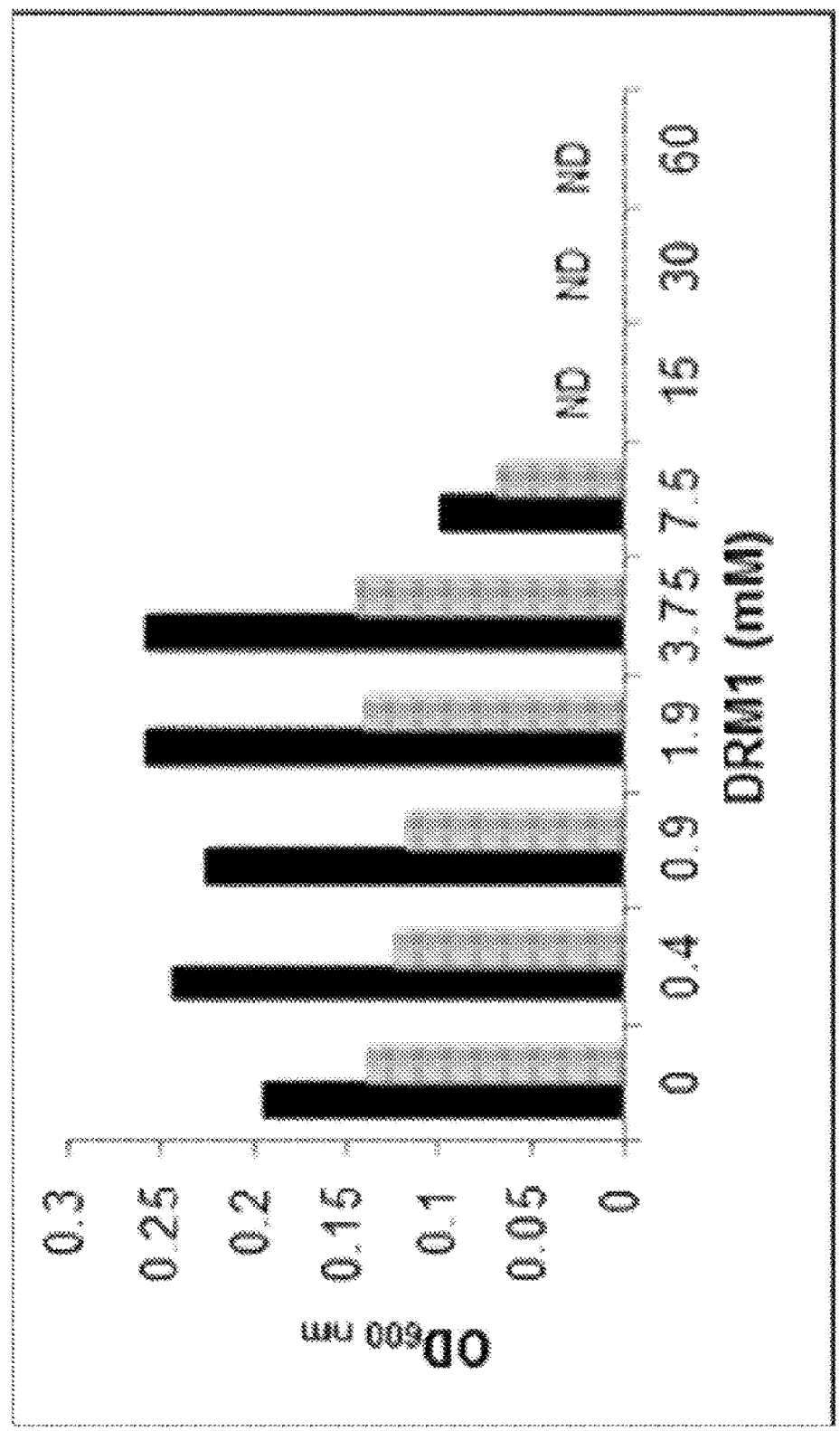
Figure 13:
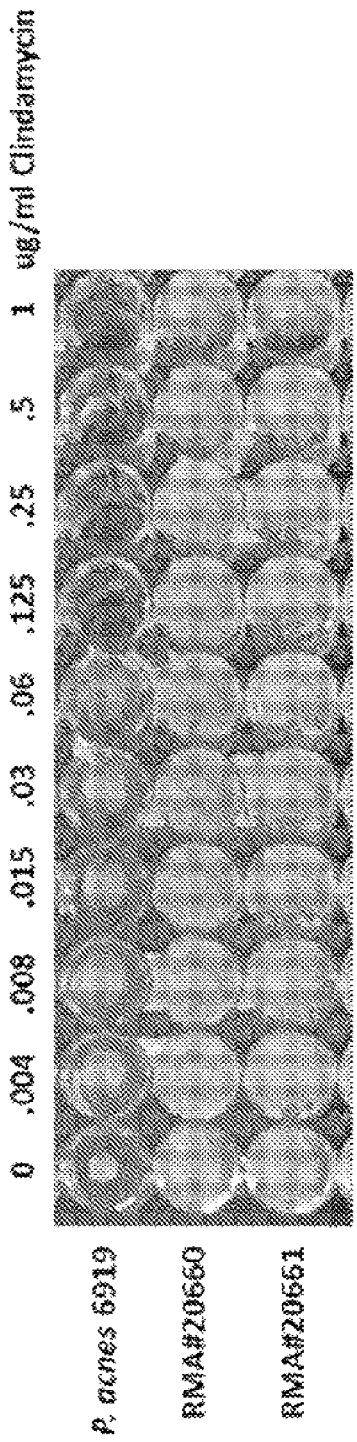
FIG. 13 illustrates that *P. acnes* strains RMA#20660 and RMA#20661 but not *P. acnes* strain 6919 were resistant to clindamycin.

Example 7—This Example Shows that DRM1 (Succinic Acid) Killed *P. Acnes* Strains that are Resistant to Antibiotics The MIC values for DRM1 (succinic acid) against multi-resistant *P. acnes* strains were determined as described in example 1. Briefly, *P. acnes* strains (RMA #20660 and RMA #20661) with low susceptibility to erythromycin, clindamycin, minocycline, and doxycycline were incubated with DRM1 (succinic acid, 0-120 mM) and the minimum inhibitory concentration was determined. As illustrated in FIGS. 12 and 13, DRM1 (succinic acid) was found to be bactericidal against antibiotic-resistant *P. acnes* strains RMA#20660 and RMA#20661. The MIC for DRM1 (succinic acid) against multi-resistant *P. acnes* strains was 15 mM. This was similar to the MIC value for non-resistant strains of *P. acnes* demonstrating that DRM1 (succinic acid) is able to kill *P. acnes* strains resistant to commonly used antibiotics.

Example 8—this Example Shows that DRM1 (Succinic Acid) Prevents Biofilm Formation DRM1 (succinic acid) prevented biofilm formation in biofilm-forming strains at a concentration of 7.5 mM and above. Biofilm formation is an important factor in *P. acnes* pathogenicity and biofilm is detected in approximately half of hair follicles of acne patients.

Figure 14:
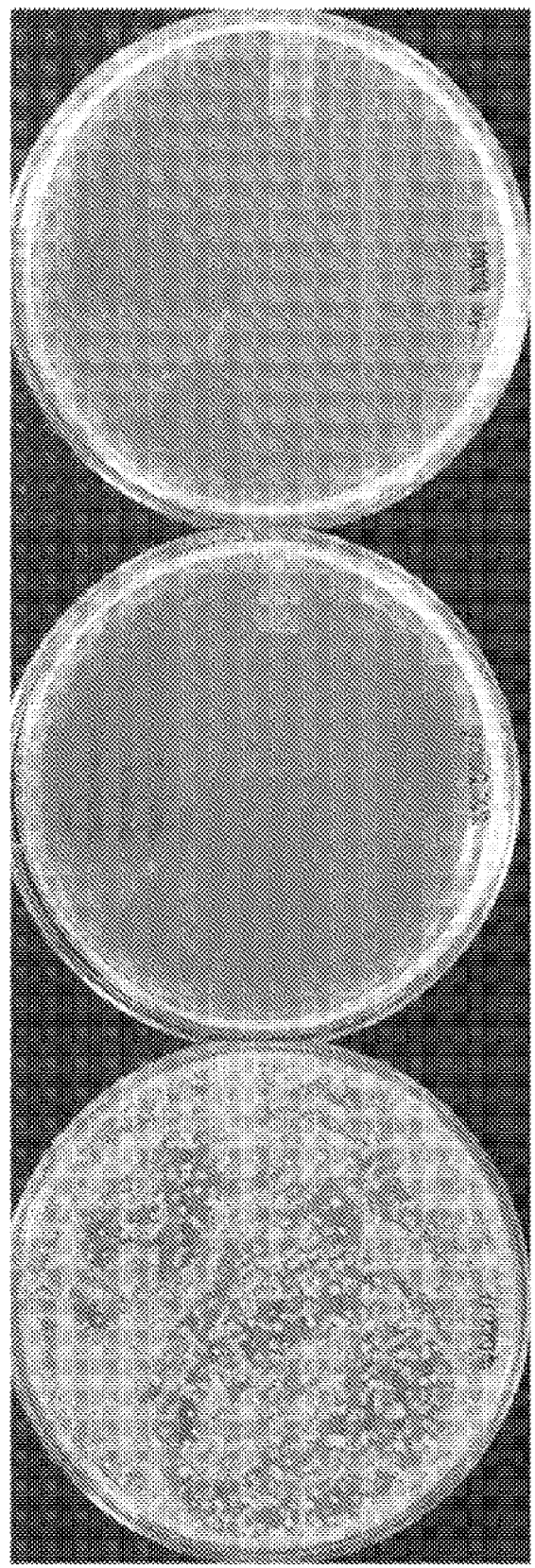
FIG. 14 shows no resistance development in the presence of DRM1 (succinic acid).

Example 9—this Example Illustrates that DRM1 (Succinic Acid) Prevents Resistance Development in *P. acnes* Strains Resistance development may be measured by two methods: single step for the determination of spontaneous frequency of resistance development and serial passage for the determination of progressive resistance development. Single step resistance frequency was determined by spreading a large inoculum of *P. acnes* ($10^9$ to $10^{10}$ CFU) onto a blood agar plate containing 4×, 8×, 16×, or 32× the MIC for DMR1 (succinic acid) as described in Example 2. The spontaneous resistance frequency was calculated from the number of colonies that grow on plates containing DRM1 vs. the number of colonies that grow on DRM1-free agar. As shown in FIG. 14, no colonies grew and therefore no resistance was detected. For progressive resistance selection, *P. acnes* (106 CFU/ml) will be exposed to a series of tubes containing serial 2-fold increasing concentrations of DRM1 (succinic acid) for a total of 10 cycles (72 hours each). The MIC of DMR1 (succinic acid) will be determined from the tubes containing the highest drug concentration. Tubes with the highest drug concentration that still shows turbidity will be used to inoculate (100 μl) a new series of tubes containing drug dilutions. To investigate whether DRM1 (succinic acid) could prevent the emergence of antibiotic resistance, experiments will be performed as described in the presence of 0.25 times the MIC of DRM1 (succinic acid). The resistance stability of each clone will be determined by sub-culturing onto drug-free agar for three cycles and determining the DRM1 (succinic acid) MIC via the microbroth dilution method as described in Example 1.

*P. acnes* strains did not develop spontaneous or progressive resistance to DMR1 (succinic acid) and including DRM1 (succinic acid) in combination with antibiotics for acne treatment prevents antibiotic resistance emergence and development.

Discussion of Examples: 6-9

Examples 6-9 illustrate that combinations with antibiotics prevents resistance development while reducing side effects.

DRM1 (succinic acid) combined with topical antibiotics can be used to replace side effect causing BPO in combinations containing antibiotics and BPO. DRM1 (succinic acid) is bactericidal. Many antibiotics are bacteriostatic which promotes resistance development. DRM1 (succinic acid) is effective against antibiotic resistant *P. acnes* strains and prevents emergence of antibiotic resistant *P. acnes* strains when used in combinations with antibiotics. In addition, DRM1 prevents biofilm formation.

Example 10: Synthetic SE Microbiome Complex

A synthetic SE Microbiome Complex (the "SE Microbiome Complex") containing a defined combination of *S. epidermis* metabolites and prebiotics was prepared by combining at least the following in a concentration of 0-10%:
1. At least one metabolite produced by *S. epidermidis* (e.g., succinic acid, acetic acid, lactic acid, butyric acid, other short chain fatty acids, other metabolites including small molecules, peptides or proteins).
2. At least one prebiotic compound (e.g., glycerol, sucrose, maltose, lactose, other carbohydrate or other compounds that supports fermentation and growth of *S. epidermidis*)

The components of the synthetic SE Microbiome Complex were produced by chemical synthesis or by microbial fermentation using wild-type or engineered microorganisms. The SE Microbiome Complex was optimized for bactericidal properties against *P. acnes*, skin tolerance, and cosmetic acceptance. The SE Microbiome Complex was formulated for use for the treatment of acne vulgaris.

Example 11: Formulation SE Microbiome Complex with Salicylic Acid for the Treatment of Acne Vulgaris Using Medicated Acne Treatment Pads Acne treatment pads formulation (Formulation 1): The formulation was prepared that contained salicylic acid (1%), organic aloe vera (50%), propanediol (15%), organic grain alcohol (10%) and SE Microbiome Complex. The SE Microbiome complex consisted of 2% succinic acid, 1% Brij L4, 1% dimethyl isosorbide ether, and 1% glycerin (prebiotic compound). Optionally, organic lemon essential oil was added to a final concentration of 0-1% and grapefruit seed extract to a final concentration of 0-1%. Sodium hydroxide was used to adjust the solution pH to 3.9-4.5. Succinic acid was prepared by microbial fermentation or by chemical synthesis. Alternatively, succinic acid in the formulation was replaced by conditioned media prepared by fermenting *S. epidermidis* as follows: *S. epidermidis* was incubated in phenol red-free rich medium with glycerol (20 g/l) for one to six days. After that, microorganisms were discarded by centrifugation at 5,000 g for 30 min. Fermented media were then passed through 0.2-μm-pore-size filters. Conditioned media contained succinic acid and other *S. epidermidis* fermentation metabolites. Alternatively, conditioned media was used in addition to succinic acid. Alternatively, glycerin was replaced by other prebiotic compound (such as sucrose, maltose, lactose or other carbohydrates and other prebiotic compounds that support the fermentation of *S. epidermidis*). Alternatively, organic components in the formulation were replaced by non-organic equivalent components. The formulated solution was poured over pads (material—rayon, Lyocell, Polyester or similar) in a container. The pads were used for applying the topical treatment for acne vulgaris.

Example 12: Formulation of a Salicylic Acid and Succinic Acid Combination for the Acne Spot Treatment of Acne Vulgaris Using a Concentrated Gel Acne spot treatment formulation (Formulation 2) was prepared containing: Salicylic acid (2%), propanediol (15%), organic grain alcohol (10-20%) and SE Microbiome Complex—super strength (consisting of 4% succinic acid, 3% Brij L4, 5% dimethyl isosorbide). Sodium hydroxide was used to adjust the solution pH to 3.9-4.5. Hydroxyethyl cellulose or eco-gel was added to gel the solution at a concentration of 1-3%. Optionally, organic tee tree essential oil (0-10%) and lemon essential oil (0-1%) was added. Optionally, organic aloe vera (0-50%) was added. Optionally, glycerin or other prebiotic compounds (0-5%) were added (such as sucrose or other carbohydrates or prebiotic compounds that support the growth/fermentation of *S. epidermidis*). Alternatively, conditioned media of fermenting *S. epidermidis* (prepared as described in Example 1) was used instead of or in addition to succinic acid. Alternatively, organic components in the formulation were replaced by non-organic equivalent components. Gel was filled into tubes for application. Gel was used for topical treatment of acne vulgaris.

Example 13: Bacterial Cultivation

*P. acnes* (ATCC 6919) was cultured on reinforced Clostridial medium (RCM) agar plates at 37° C. under anaerobic conditions using a Gas-Pak (BD). For each assay, an inoculum of *P. acnes* was prepared by suspending a colony of *P. acnes* in 5 mL RCM and growing at 37° C. under anaerobic conditions for 72 hours. Cultures were harvested, washed with PBS and resuspended in fresh, sterile RCM broth to a concentration of $2 \times 10^6$ CFU/ml.

Example 14: Formulation 1 and Formulation 2 are Inhibitory Against *P. acnes*

Figure 15:
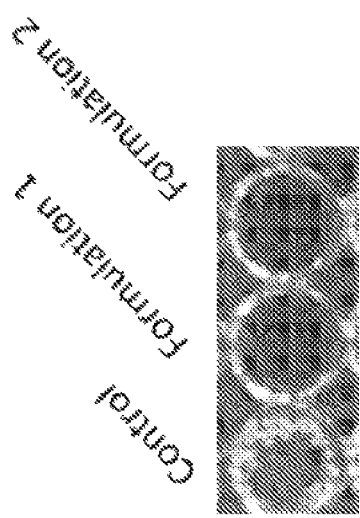
FIG. 15 shows that Formulation 1 and Formulation 2 inhibit *P. acnes* growth.

Formulation 1 (Example 11) and Formulation 2 (Example 12) was incubated in 96-well plate with *P. acnes* prepared as described in Example 13. Control sample contained *P. acnes* in media only. Plates were incubated under anaerobic conditions using a Gas-Pak (BD) for 72 hours at 37° C. Following incubation, the plate was examined visually. Control samples exhibited growth as expected. No growth was observed in wells containing Formulation 1 and Formulation 2 (FIG. 15). The MIC (determined by serial dilutions) was determined to be at 0.015% succinic acid for Formulation 1 and Formulation 2.

Example 15: Formulation 1 and Formulation 2 is Bactericidal Against *P. acnes*

The minimal bactericidal concentration for each formulated drug was determined according to the Clinical Laboratory Standards Institute (CLSI) document M26-A. Sample wells from the MIC assay in Example 14 were serially diluted 1:10 to 1:10$^4$ in PBS and each dilution (5 μl) was plated on RCM agar plates.

Figure 16:
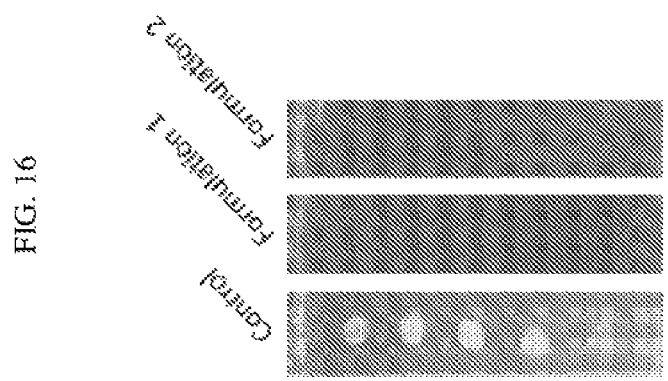
FIG. 16 shows that Formulation 1 and Formulation 2 are bactericidal against *P. acnes*.

The plates were incubated at 37° C. in a Gas-Pak. Following incubation, Formulation 1 (from Example 11) and Formulation 2 (from Example 12) exhibited no growth (FIG. 16). Control samples exhibited growth as expected. MBC concentration was determined as a concentration that shows a ≥3 log$_{10}$ decrease in bacterial growth. The results showed that Formulation 1 and Formulation 2 are bactericidal against *P. acnes*. Using serial dilutions, the MBC was determined to be 0.015% succinic acid for Formulation 1 and 0.015% succinic acid for Formulation 2.

Example 16: Production of SE Microbiome Complex by *S. epidermidis* Fermentation with Prebiotic Compounds and Testing Against *P. acnes*

This example illustrates the growth inhibitory effects of *S. epidermidis* conditioned media prepared with various prebiotics against *P. acnes*.

Preparation of Prebiotics: Glycerol, sucrose, β-lactose, and D-(+)-maltose were purchased from Sigma-Aldrich. Stock solutions of each prebiotic (4% w/v) were prepared in water and filtered through a 0.22 μm filter for sterilization.

Preparation of *S. epidermidis* conditioned media: *S. epidermidis* (ATCC 12228) was cultured on trypic soy broth (TSB) agar plates at 37° C. For each assay, an inoculum of *S. epidermidis* was prepared by suspending one colony of *S. epidermidis* from a TSB agar plate into 7 ml of TSB broth and growing at 37° C., 215 RPM for 16 hours. The overnight culture was subcultured by adding 100 μl of overnight culture to 10 ml of fresh TSB. Once mid-log phase was reached, the cells were pelleted by centrifugation, washed with PBS and resuspended in fresh PBS. In 15 ml culture tubes, 4.9 ml of Rich Broth (20 g/L yeast extract, 6 g/L TSB) was combined with 40 μl 0.5% phenol red indicator, 5 ml of 4% prebiotic (glycerol, sucrose, β-lactose, or D-(+)-maltose) or PBS as a control, and *S. epidermidis* (10$^5$ CFU/ml) and placed in an anaerobic Gas-Pak (BD). The cultures were incubated at 37° C., 215 RPM for 6 days. Following fermentation, the cells were pelleted and the supernatants were filtered through a 0.22 μm filter for sterilization.

Minimum Inhibitory Concentration (MIC) Determination: Individual MIC values were determined for each conditioned medium according to the microbroth dilution method. *P. acnes* (ATCC 6919) was cultured in RCM broth and harvested during mid-log phase of growth. The bacterial pellet was washed and resuspended in PBS. A stock of *P. acnes* (10$^7$ CFU/ml) was prepared using the estimation that an OD600 nm of 1.0 corresponds to about 10$^7$ CFU/ml. Two-fold serial dilutions of each conditioned medium (90 μl) in PBS were added to wells in a 96-well plate followed by 10 μl of the prepared *P. acnes* inoculum. Conditioned media without *P. acnes* and RCM medium with *P. acnes* only were used for negative and positive controls, respectively. Plates were incubated under anaerobic conditions using a Gas-Pak (BD) for 48 hours at 37° C. Following incubation, each well was resuspended by pipetting and the optical density at 600 nm (OD600) was determined on a plate reader. The MIC value was defined as the first well showing ≥90% reduction in growth compared to controls.

Fermentation of prebiotics by *S. epidermidis*: FIG. 17 shows *S. epidermidis* cultures grown with (a) PBS, (b) glycerol, (c) β-lactose, (d) maltose, (e) sucrose under anaerobic conditions. After growing for six days under anaerobic conditions, the *S. epidermidis* cultures containing glycerol, sucrose, D-(+)-maltose and β-lactose showed a change of color from red to yellow indicating the acidification of the media when compared to the PBS control. No change in color occurred in PBS control (a). The acidification of the media was due to the formation of short chain fatty acid (e.g., succinic acid, acetic acid, lactic acid, butyric acid) resulting from the fermentation of prebiotics by *S. epidermidis*. The glycerol sample was not as bright of a yellow compared to the other three prebiotics and still had a tint of pink. This indicates that sucrose, maltose and galactose prebiotics showed the most efficient fermentation and highest production of short chain fatty acids and therefore these are the preferred prebiotics to use in formulations for the treatment of acne.

*P. acnes* growth inhibition by *S. epidermidis* conditioned media: Conditioned media prepared by fermentation in the presence of prebiotics—glycerol, sucrose, D-(+)-maltose and β-lactose under anaerobic condition were able to inhibit *P. acnes* growth (undiluted media was the MIC). RCM control media prepared in the absence of prebiotics were not inhibitory.

Example 17: Skin Tolerability and Cosmetic Acceptance Testing

Formulation 1 and Formulation 2 with and without aloe vera was tested in human volunteers for skin tolerability and cosmetic acceptance. Evaluation was performed by using questionnaire and a scoring system. Score of 1-5 was used. Score 1 for skin tolerability corresponded to irritation, skin reddening. Score 5 for skin tolerability corresponded to no adverse reaction and excellent tolerability. Score 1 for cosmetic acceptability corresponded to unacceptable product due to smell and feel. Score 5 for cosmetic acceptability represented excellent cosmetic acceptability (smell and feel). Commercially available products were used as controls. Results are recorded in table 1. Results indicate that addition of aloe vera significantly improves skin tolerability and that Formulation 1 and Formulation 2 have significantly improved cosmetic acceptance (smell and feel) compared to commercially available products.

TABLE 7

Skin tolerability and cosmetic acceptance scores

| Formulation | Skin tolerability score | Cosmetic acceptance score |
|---|---|---|
| Formulation 1 with aloe vera | 5 | 5 |
| Formulation 1 without aloe vera | 4 | 4 |
| Commercially available acne treatment pads with salicylic acid 1% | 3 | 1 |
| Formulation 2 | 5 | 5 |

Example 18: Testing of Treatments Containing Combinations Products in Human Subjects Formulation 1 (Example 11) and Formulation 2 (Example 12) were tested in human subjects. The Formulation 1 was applied using Acne Treatment Pads one or two times per day. Improvement in acne symptoms was observed (FIG. 18, panel A vs. panels B and C). Panel A shows acne lesions prior to treatment, panels B and C show disappearance of acne lesions post treatment with Formulation 1. Formulation 2 (Acne Spot Treatment gel) was used as a spot treatment on individual acne lesions in human subjects. The subjects reported reduction in pain and inflammation in 5-10 minutes post application, significantly faster healing of acne lesions compared to benzoyl peroxide and lack of hyperpigmentation (dark spot side effect observed when benzoyl peroxide was used). When Acne Spot Treatment was used in combination with hydrocolloid Acne Pimple Patches, the healing of acne lesions was visible in less than a day.

Example 19: Five Step Acne Treatment System Using Combination of Topical Treatment Containing SE Microbiome Complex, Oral Probiotics and Oral Supplements The five step treatment system combined the topical treatment containing SE Microbiome Complex with oral probiotics and oral supplements (such as zinc). Oral probiotics contained a diverse combination of probiotic strains of 500 million-30 billion CFUs/capsule. The combination of probiotic strains included any combination of *Bifidobacterium lactis, Bifidobacterium longum, Bifidobacterium bifidum, Bifidobacterium breve, Bifidobacterium infantis, Lactobacillus acidophilus, Lactobacillus rhamnosus, Lactobacillus salivarius, Lactobacillus plantarum, Lactobacillus bulgaricus, Lactobacillus casei, Lactococcus lactis*, or additional probiotic strains and optionally contained prebiotics (such as FOS or Arabinogalactan).

Five step treatment system consisted of:

Step 1: Washing face in the morning and evening.

Step 2: Applying Acne Treatment Pads (Formulation 1 from Example 11) to affected areas and Acne Spot Treatment (Formulation 2 from Example 12) to individual pimples.

Step 3: Covering whiteheads and inflamed pimples with Acne Pimple Patches (containing hydrocolloid) to treat blemishes overnight.

Step 4: Taking Probiotics (1-3 times daily) and 25-50 mg Zinc (1 time daily with a meal).

Step 5: Repeating for at least 2 months.

Compared to subjects using only topical products, the subjects who used topical products in combination with oral probiotics and zinc achieved improvement in acne symptoms.

Example 20: Combination Products Containing Retinoids

This example will be performed to screen combinations of DRM1 and retinoids (tretinoin, adapalene, tazarotene, isotretinoin, retinyl palmitate, retinol, or retinaldehyde) for antimicrobial and anti-inflammatory properties, and to determine if the compounds can decrease the amount of acne lesions in acne.

The minimal inhibitory concentration (MIC) and minimum bactericidal concentration of combinations of DRM1 and retinoids will be determined to monitor the growth inhibitory effects of the combination. To determine the MIC values, DRM1 will be analyzed in concentrations ranging from 1-100 mM and the retinoids will vary in concentrations from 0.025%-0.1%. Two-fold serial dilutions of the DRM1-retinoid combination will be made in PBS (50 µl). An inoculum of $2 \times 10^6$ CFU/ml *P. acnes* in RCM will be prepared and 50 µl will be added to the wells containing the DRM1-retinoid combinations.

Bactericidal properties of the DRM1 and retinoid combinations will be analyzed using the time-kill assay. Briefly, 0.4 ml of 10× the desired final concentration of DRM1 and retinoid will be added to 2.8 ml RCM broth along with 0.4 ml of $10^7$ CFU/ml *P. acnes*. Media with *P. acnes* only will be used for a positive control. A separate tube will be prepared for each time point for all measured concentrations of the DRM1-retinoid combination. The assay will be performed under anaerobic conditions at 37° C. The reaction will be analyzed after 0, 0.5, 1, 2, 4, 8, and 24 hours. At each time point the corresponding tube will be removed and the sample will be diluted 1:10 to $1:10^5$ in PBS. Each dilution will be spotted (10 µl) in triplicate on RCM agar plates and incubated under anaerobic conditions using a Gas-Pak (BD) for 4-7 days at 37° C. Following incubation, the plate will be visually examined and the bacterial counts for each time point will be determined.

The best in vitro performing DRM1-retinoid combination, as determined by the MIC assay and time-kill assay, will be formulated into a topical cream, gel, or solution applied with pads. The topical formulation will be applied to acne infected areas twice a day (morning and night) following cleansing of the skin.

It is expected that the application of a DRM1-retinoid combination to acne infected skin will decrease the acne lesion counts when compared to controls—placebo, DRM1 alone or retinoid alone. It is expected that the count of both inflammatory and non-inflammatory lesions will decrease compared to controls.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Other publications incorporated herein by reference in their entirety include:

Wang Y (1), Kuo S, Shu M, Yu J, Huang S, Dai A, Two A, Gallo R L, Huang C M. *Staphylococcus epidermidis* in the human skin microbiome mediates fermentation to inhibit the growth of *Propionibacterium acnes*: implications of probiotics in acne vulgaris. Appl Microbiol Biotechnol. 2014 January; 98(1):411-24. doi: 10.1007/s00253-013-5394-8. Epub 2013 Nov. 22.

What is claimed is:

1. A method of killing a *Propionibacterium acnes* (*P. acnes*) that is resistant to an antibiotic, the method comprising treating the *P. acnes* with a composition comprising a combination of salicylic acid and succinic acid present in a 1:2 ratio to produce a synergistic effect in treating acne vulgaris, wherein the *P. acnes* is resistant to erythromycin, clindamycin, minocycline, doxycycline, or any combination thereof.

2. The method of claim 1, wherein the *P. acnes* is on skin of a subject having acne vulgaris and the composition is a topical composition.

3. The method of claim 1, wherein the composition further comprises azelaic acid.

4. The method of claim 1, wherein the composition further comprises picolinic acid.

5. The method of claim 1, wherein the composition further comprises benzoyl peroxide.

6. The method of claim 1, wherein the composition further comprises an antibiotic.

7. The method of claim 1, wherein the salicylic acid is present at a concentration from 0.1 to 5%.

8. The method of claim 1, wherein the succinic acid is present at concentration from 0.1 to 10%.

9. The method of claim 2, wherein the topical composition further comprises aloe vera, propanediol, grain alcohol, lemon essential oil, and grapefruit seed extract.

10. The method of claim 2, wherein the topical composition further comprises aloe vera (0-50 w/w %), propanediol (15 w/w %), grain alcohol (10-20 w/w %), lemon essential oil (0-1 w/w %), grapefruit seed extract (0-1 w/w %), sodium hydroxide to adjust the solution pH to 3.9-4.5, and SE Microbiome Complex.

11. The method of claim 2, wherein the topical composition further comprises SE Microbiome complex.

12. The method of claim 11, wherein the SE Microbiome complex comprises 0.5-4 w/w % succinic acid, 1-5 w/w % dimethyl isosorbide, and 0-5 w/w % carbohydrate-based prebiotic agent.

13. The method of claim 11, wherein the SE Microbiome complex comprises at least one of acetic acid, lactic acid, butyric acid, or a short chain fatty acid, and at least one of glycerol, sucrose, maltose, or lactose.

14. The method of claim 2, wherein the topical composition further comprises a gelling agent.

15. The method of claim 2, wherein the topical composition is applied to the skin of the subject on a pad.

16. The method of claim 2, wherein the topical composition is applied to the skin of the subject from a tube.

* * * * *